United States Patent [19]
Blume

[11] Patent Number: 6,152,887
[45] Date of Patent: Nov. 28, 2000

[54] METHOD AND TEST KIT FOR ORAL SAMPLING AND DIAGNOSIS

[76] Inventor: Richard Stephen Blume, 240 Main St., Northport, N.Y. 11768

[21] Appl. No.: 09/031,578

[22] Filed: Feb. 27, 1998

[51] Int. Cl.⁷ ..................................................... A61B 5/00
[52] U.S. Cl. ........................................... 600/573; 604/317
[58] Field of Search .................................... 600/573, 576, 600/581; 604/317

[56] References Cited

U.S. PATENT DOCUMENTS

| | | |
|---|---|---|
| 4,114,605 | 9/1978 | McGhee et al. . |
| 4,321,251 | 3/1982 | Mashberg . |
| 4,397,944 | 8/1983 | Komura . |
| 4,418,702 | 12/1983 | Brown et al. . |
| 5,022,409 | 6/1991 | Goldstein et al. . |
| 5,103,386 | 4/1992 | Goldstein et al. . |
| 5,339,829 | 8/1994 | Thieme et al. . |
| 5,479,937 | 1/1996 | Thieme et al. . |
| 5,563,073 | 10/1996 | Titmas . |
| 5,573,009 | 11/1996 | Thieme et al. . |
| 5,786,227 | 7/1998 | Charlton .................................. 600/573 |

OTHER PUBLICATIONS

Singh, S. et al., "Determinants of esophageal 'alkaline' pH environment in controls and patients with gastroesophageal reflux disease," *Gut*, 1993 Mar.; 34(3): 309–16.
Chen, M., et al., "Gastroesphageal reflux disease: correlation of esophageal pH testing and radiographic findings," *Radiology*, 1992; 185: 483–6.
Kahrilas, P., "Gastroesophageal reflux disease," *JAMA*, Sep. 25, 1996; 276(12): 983–8.
Schoeman et al., "Mechanisms of gastroesophageal reflux in ambulant healthy human subjects," *Gastroenterology*, 1995 Jan.; 108(1): 83–91.
Richter, J., "Extrasophageal presentations of gastroesophageal reflux disease," *Semin. Gastrointest. Dis.*, 1997 Apr.; 8(2): 75–89.
Wall Street Journal, "When your heartburn starts to linger after the holidays," Dec. 29, 1997.
Wiener, G., et al., "Chronic hoarseness secondary to gastroesophageal reflux disease: documentation with 24–hour ambulatory pH monitoring," *Am. J. Gastroenterol.*, 1989; 84(12): 1503–8.
Contencin, P., and Narcy, P., "Gastroesophageal reflux in infants and children: A pharyngeal pH monitoring study," *Arch. Otolaryngol. Head Neck Surg.*, 1992 Oct.; 118: 1028–30.
Pope, C., "Acid–reflux disorders," *N. Engl. J. Med.*, Sep. 8, 1994; 331(10): 656–60.
Meurman, J., et al., "Oral and dental manifestations in gastroesophageal reflux disease," *Oral Surg. Oral Med. Oral Pathol.*, 1994 Nov.; 78(5): 583–9.
Schroeder, P., et al., "Dental erosion and acid reflux disease," *Ann. Intern. Med.*, Jun. 1, 1995; 122(11): 809–15.
Madinier, I., et al., "Oral carriage of Helicobacter pylori: a review," *J. Periodontal.*, 1997 Jan.; 68(1):2–6.
Schindlbeck, N., et al., "Which pH threshold is best in esophageal pH monitoring?" *Am. J. Gastroenterol.*, 1991; 86(9): 1138–41.

(List continued on next page.)

Primary Examiner—Cary O'Connor
Assistant Examiner—Pamela S. Wingood

[57] ABSTRACT

A non-invasive, non-instrumented method and test kit for oral sampling and subsequent rapid or point-of-care sample analysis and diagnosis, including pH determination for detecting the presence and extent of gastroesophageal (acid) reflux. The test for acid reflux includes sampling of the pharynx by gargling with specified liquid (10) and then retrieving the resulting fluid and measuring its pH. The invention may be used both for rapid self-testing in the home as well as for point-of-care diagnosis by health professionals. A test kit for obtaining an oral sample contains an article (16) for measuring the sampling liquid (10) for gargling, a container (12) for depositing the sampling liquid (10) after gargling, a horizontal line (14) provided thereon to serve as an indicator that an adequate volume of gargled sampling liquid (10) was collected, and diagnostic tools (18, 20, 22, 24) for identification of a characteristic of interest, such as pH, of the retrieved sampling liquid (10) within the collection container (12) at the time of retrieval.

10 Claims, 2 Drawing Sheets

OTHER PUBLICATIONS

Orr, W., et al., "The pattern of nocturnal and diurnal esophageal acid exposure in the pathogenesis of erosive mucosal damage," *Am. J. Gastroenterol.,* 1994 Apr.; 89(4): 509–12.

Jacob, P., et al., "Proximal esophageal pH–metry in patients with reflux laryngitis," *Gastroenterology,* 1991; 100: 305–10.

Shaker, R., et al., "Esophagopharyngeal distribution of refluxed gastric acid in patients with reflux laryngitis," *Gastroenterology,* 1995; 109: 1575–82.

Vaezi, M., and Richter, J., "Twenty–four hour ambulatory esophageal pH monitoring in the diagnosis of acid reflux–related chronic cough," *South Med. J.,* 1997 Mar.; 90(3): 305–11.

Koufman, J., and Cummins, M., "The prevalence and spectrum of reflux in laryngology: a prospective study of 132 consecutive patients with laryngeal and voice disorders," *Center for Voice Disorders of Wake Forest University,* 1997.

Locke, III, G., et al., "Prevalence and clinical spectrum of gastroesophageal reflux: A population–based study in Olmsted County, Minnesota," *Gastroenterology,* 1997; 112: 1448–56.

Isolauri, J., et al., "Natural course of gastroesophageal reflux disease: 17–22 year follow–up of 60 patients," *Am. J. Gastroenterol.,* 1997 Jan.; 92(1): 37–41.

Olden, K., and Triadafilopoulos, G., "Failure of initial 24–hour esophageal pH monitoring to predict refractoriness and intractability of reflux esophagitis," *Am. J. Gastroenterol.,* 1991; 86(9): 1142–6.

Jamieson, J., et al., "Ambulatory 24–hour esophageal pH monitoring: normal values, optimal thresholds, specificity, sensitivity, and reproducibility," *Am. J. Gastroenterol.,* 1992; 87(9): 1102–1110.

Tew, S., et al., "The illness behavior of patients with gastroesophageal reflux disease with and without endoscopic esophagitis," *Dis. Esophagus.,* 1997 Jan.; 10(1): 9–15.

Bardhan, K., "Is there any acid peptic disease that is refractory to proton pump inhibitors?" *Aliment. Pharmacol. Ther.,* 1993; 7 Suppl 1: 13–24.

Sachs, G., "Proton pump inhibitors and acid–related diseases," *Pharmacotherapy,* 1997 Jan.–Feb.; 17(1): 22–37.

Sontag, S., et al., "Lansoprazole heals erosive reflux esophagitis resistant to histamine H2–receptor antagonist therapy," *Am. J. Gastroenterol.,* 1997 Mar.; 92(3): 429–37.

Shaw, G., et al., "Subjective, laryngoscopic, and acoustic measurements of laryngeal reflux before and after treatment with omeprazole," *J. Voice.,* 1996 Dec.; 10(4): 410–8.

Devault, K. and Castell, D., "Guidelines for the diagnosis and treatment of gastroesophageal reflux disease," *Arch. Intern. Med.,* 1995; 155(20): 2165–2173.

Haase, G., et al., "A unique teletransmission sytem for extended four–channel esophageal pH monitoring in infants and children," *J. Ped. Surg.,* 1987 Jan.; 22(1): 68–74.

Contencin, P., et al., "Measurement of pH of the rhinopharynx in children with gastroesophageal reflux," *Presse Medicale,* 1989; 18(1): 13–6.

Joshi, G., et al., "Continuous hypopharyngeal pH measurement in spontaneously breathing anesthetized outpatients: laryngeal mask airway versus tracheal intubation," *Anesth. Analg.,* 1996; 82: 254–7.

Ayre, J., "The gargle test: new oral cancer screening method," *NY State Dent. J.,* 1972 Jun.–Jul.; 38(6): 345–50.

Loughlin, C., and and Koufman, J., "Paroxysmal laryngospasm secondary to gastroesophageal reflux," *Laryngoscope,* 1996 Dec.; 106(12 Pt. 1):1502–1505.

METHOD AND TEST KIT FOR ORAL SAMPLING AND DIAGNOSIS

BACKGROUND OF THE INVENTION

1. Field of the Invention

The present invention relates generally to health care diagnostics and specifically to a method and a test kit for non-invasive, non-instrumented oral sampling in a human subject utilizing the collection of fluid from the mouth and/or pharynx of the patient. Fluid obtained from the mouth through rinsing, and/or from the pharynx (throat area) through gargling, is collected; analysis of the characteristic of interest in the fluid is performed in the specified collection device, providing a rapid result without manual handling of the fluid sample. The methods of the invention are suitable for a self-test (test performed in the home) and as a point-of-care test performed by the health professional to provide a rapid result in a clinical setting. The methods of the invention may be applied to any characteristic of the mouth and/or pharynx which can be sampled by rinsing and/or gargling, retrieving the resulting fluid in a specified collection container or device and then analyzing the fluid in the collection container or device to provide a rapid or point-of-care result.

More particularly, the present invention provides methods and a test kit for non-invasive, non-instrumented assessment and diagnosis of the condition of acid reflux by sampling of the pharynx through the gargling process, and rapid determination of the pH of the collected fluid.

The use of diagnostic procedures or tests which provide rapid results in the health professional's office (point-of-care testing) has become an important component of medical practice. Such procedures are typically non- or minimally-invasive, require limited or no instrumentation and allow for efficient and cost-effective diagnosis. The development of rapid, non-invasive and non-instrumented technologies has increased the availability of consumer "home test" kits, allowing for layperson self-testing to identify important health conditions (e.g., pregnancy, blood in the stool, elevated cholesterol) and to promote appropriate and timely use of health care resources.

Gastroesophageal or acid reflux (hereinafter referred to as acid reflux) is the retrograde movement of acidic contents of the stomach into the esophagus and beyond. The body manages minor amounts of acid reflux, which are common in normal gastrointestinal function, by mechanical movement back toward the stomach in the normal direction of ingested food and liquid (known as peristalsis) and by neutralization by bicarbonate sources, including saliva (Singh, S. et al., "Determinants of esophageal 'alkaline' pH environment in controls and patients with gastroesophageal reflux disease," *Gut*, March 1993; 34 (3): 309–16). As a result, the pH levels of tissues affected by minor amounts of acid reflux are maintained at normal levels. However, increased amounts of acid reflux overwhelm these corrective factors, resulting in greater acidity of affected tissues and the resulting symptoms of acid reflux. While the lining of the stomach is normally able to resist the adverse effects of stomach acid, this is not the case for tissues contacted by acid reflux including the esophagus and pharynx. Reduced saliva volume and/or neutralization potential can contribute to increased acidity of the pharynx during periods of sleep (known as nocturnal pharyngeal acidification).

Acid reflux is considered to be the most common inflammatory disorder of the upper gastrointestinal tract (Chen, M., et al., "Gastroesophageal reflux disease: correlation of esophageal pH testing and radiographic findings," *Radiology*, 1992; 185: 483–6) and is estimated to affect over 15 million Americans on a daily basis, and 40% of the population on a monthly basis (Kahrilas, P., "Gastroesophageal reflux disease," JAMA. Sep. 25, 1996 25; 276(12): 983–8 and American College of Gastroenterology, 1997). Acid reflux occurs most frequently within the first 3 hours after food intake (Schoeman et al., "Mechanisms of gastroesophageal reflux in ambulant healthy human subjects," *Gastroenterology*, January 1995; 108(1): 83–91). Exposure of tissues to acid reflux results in symptoms including regurgitation, heartburn and sore throat and may lead to tissue damage. Symptoms and tissue damage caused by acid reflux are referred to in the medical profession as gastroesophageal reflux disease (GERD).

The occurrence of extraesophageal effects of acid reflux (effects outside the esophagus, i.e., in the pharynx or throat) due to acid reflux reaching to this area is increasingly being recognized in the medical community today (Chen et al, 1992, supra; Richter, J., "Extraesophageal presentations of gastroesophageal reflux disease," *Semin. Gastrointest. Dis.* April 1997; 8(2): 75–89; and *Wall Street Journal*, "When your heartburn starts to linger after the holidays," Dec. 29, 1997). This causes various problems including hoarseness, laryngitis and chronic cough (Wiener, G., et al., "Chronic hoarseness secondary to gastroesophageal reflux disease: documentation with 24-hour ambulatory pH monitoring," *Am J Gastroenterol.*, 1989; 84(12): 1503–8; Contencin, P., and Narcy, P., "Gastroesophageal reflux in infants and children: A pharyngeal pH monitoring study," *Arch. Otolaryngol. Head Neck Surg.*, October 1992; 118:1028–30; Pope, C., "Acid-reflux disorders," *N. Engl. J. Med.*, Sep. 8. 1994; 331(10): 656–60; and Kahrilas, 1996, supra). Because it may at times reach the mouth, acid reflux has been observed to have effects on this area as well (Meurman, J., et al., "Oral and dental manifestations in gastroesophageal reflux disease," *Oral Surg. Oral Med. Oral Pathol.*, November 1994; 78(5): 583–9; Schroeder, P., et al., "Dental erosion and acid reflux disease," *Ann. Intern. Med.*, Jun. 1, 1995; 122(11): 809–15; and Madinier, I., et al., "Oral carriage of Helicobacter pylori: a review," *J. Periodontol.*, January 1997; 68(1):2–6). The occurrence of acid reflux reaching the pharynx and altering the pH of contacted tissues provides a basis for sampling of the pharynx to detect the acid reflux condition. Prior to the present invention, only instrumented, invasive methods were available to detect acid reflux.

Acid reflux causes a reduction in pH (increased acidity) of affected tissues. Detection of the pH of these tissues, including the esophagus and pharynx, provides a means for objective diagnosis of acid reflux states. Measurement of pH in the esophagus or pharynx using invasive instruments (the sole method of pH measurement in acid reflux until the present invention) has determined that decreased pH (or greater acidity) is associated with acid reflux and that decreased pH increases the risk of complications of acid reflux including esophageal erosion, laryngitis and chronic cough (Schindlbeck, N., et al., "Which pH threshold is best in esophageal pH monitoring?" *Am. J. Gastroenterol.*, 1991; 86(9): 1138–41; Chen et al., 1992, supra; Orr, W., et al., "The pattern of nocturnal and diurnal esophageal acid exposure in the pathogenesis of erosive mucosal damage," *Am. J. Gastroenterol.*, April 1994; 89(4): 509–12; Jacob, P., et al., "Proximal esophageal pH-metry in patients with reflux laryngitis," *Gastroenterology* 1991; 100: 305–10; Shaker, R., et al., "Esophagopharyngeal distribution of refluxed gastric acid in patients with reflux laryngitis," *Gastroenterology* 1995; 109: 1575–82; and Vaezi, M., and Richter, J., "Twenty-four hour ambulatory esophageal pH monitoring in the diagnosis of acid reflux-related chronic cough," *South Med.J.*, March 1997; 90(3): 305–11). Using instrument monitoring, 50 percent of adult ear-nose-throat patients and 93 percent of children with respiratory conditions were found to have abnormal amounts of acid reflux reach to the level of the pharynx (Koufman, J., and Cummins, M., "The prevalence and spectrum of reflux in laryngology: a prospective study of 132 consecutive patients with laryngeal and voice disorders," *Center for Voice Disorders of Wake Forest University*, 1997).

The majority of persons with acid reflux symptoms do not seek professional medical evaluation and engage in self-treatment with widely-available over-the-counter medications (Locke III, G., et al., "Prevalence and clinical spectrum of gastroesophageal reflux: A population-based study in Olmsted County, Minn.," *Gastroenterology*, 1997; 112: 1448–56). These medications include antacids and drugs to reduce stomach acid production. However, while symptoms of acid reflux can be intermittent and may respond to over-the-counter medications, the condition often requires professional medical evaluation and treatment (Isolauri, J., et al., "Natural course of gastroesophageal reflux disease: 17–22 year follow-up of 60 patients," *Am. J. Gastroenterol.*, January 1997; 92(1): 37–41). Perceived symptoms can be an unreliable indicator of the presence and extent of acid reflux (Olden, K., and Triadafilopoulos, G., "Failure of initial 24-hour esophageal pH monitoring to predict refractoriness and intractability of reflux esophagitis," *Am. J. Gastroenterol.*, 1991; 86(9): 1142–6; Jamieson, J., et al., "Ambulatory 24-hour esophageal pH monitoring: normal values, optimal thresholds, specificity, sensitivity, and reproducibility," *Am. J. Gastroenterol.*, 1992; 87(9): 1102–1110; and Tew, S., et al., "The illness behavior of patients with gastroesophageal reflux disease with and without endoscopic esophagitis," *Dis. Esophagus.*, January 1997; 10(1): 9–15). Without benefit of objective assessment, symptoms of acid reflux may be confused with other gastrointestinal conditions or other health problems which require professional medical evaluation, such as chest pain.

Effective acid reflux treatment requires accurate diagnosis. Many persons do not experience sufficient acid reduction with over-the-counter treatments and doses and therefore should receive medical evaluation and prescription medication (Bardhan, K., "Is there any acid peptic disease that is refractory to proton pump inhibitors?" *Aliment. Pharmacol. Ther.*, 1993; 7 Suppl 1: 13–24). The class of acid reflux prescription medications known as proton pump inhibitors can render superior results in treatment of acid reflux (Loughlin, C., and and Koufman, J., "Paroxysmal laryngospasm secondary to gastroesophageal reflux," *Laryngoscope*, December 1996; 106(12 Pt. 1):1502–1505; Kahrilas, 1996, supra; Sachs, G., "Proton pump inhibitors and acid-related diseases," *Pharmacotherapy* January-February 1997; 17(1): 22–37; Sontag, S., et al., "Lansoprazole heals erosive reflux esophagitis resistant to histamine H2-receptor antagonist therapy," *Am. J. Gastroenterol.*, March 1997; 92(3): 429–37; and Koufman and Cummins, 1997, supra). Eighty-five percent of persons with laryngitis caused by acid reflux respond to omeprazole, a type of proton pump inhibitor (Shaw, G., et al., "Subjective, laryngoscopic, and acoustic measurements of laryngeal reflux before and after treatment with omeprazole," *J. Voice.*, December 1996; 10(4): 410–8). To ensure appropriate use of health care resources and effective treatment of acid reflux conditions, objective diagnosis is needed. Yet because of the limitations of current diagnostic methods, which involve invasive instruments, require prolonged testing and cannot be easily repeated, the large proportion of the general population which suffers with acid reflux is precluded from objective diagnostic evaluation (DeVault, K. and Castell, D., "Guidelines for the diagnosis and treatment of gastroesophageal reflux disease," *Arch. Intern. Med.*, 1995; 155(20): 2165–2173).

What is therefore needed in the art is a non-invasive, non-instrumented means of objective detection of acid reflux which provides rapid results as a point-of-care diagnostic test. Such a test could be used by medical professionals for cost-effective screening of patients for acid reflux, bringing the benefits of objective diagnosis of acid reflux to the general population. These test characteristics would also provide the means for a self-test, as test procedures would not require professional assistance. Such a test could be used to enhance self-treatment, by assisting the layperson in evaluating the cause of symptoms, tracking response to treatment and identifying a need for professional medical evaluation. Such a test would be well received in the medical community and consumer market for self-testing. The expanding array of over-the-counter options for self-treatment of acid reflux, which in the future may include potent proton-pump inhibitors, further points to the importance of objective assessment of this condition to ensure appropriate treatment and professional medical evaluation when indicated.

2. Description of the Prior Art

Previous studies have used invasive instruments to measure the pH of the pharynx area to detect acid reflux. Instrument-based pH monitoring of the pharynx has shown results in a pH range of around 5 to 7.5 (Haase, G., et al., "A unique teletransmission system for extended four-channel esophageal pH monitoring in infants and children," *J. Ped. Surg.*, January 1987; 22(1): 68–74; Contencin, P., et al., "Measurement of pH of the rhinopharynx in children with gastroesophageal reflux," *Presse Medicale*, 1989; 18(1): 13–6; Wiener et al, 1989, supra; and Chen et al, 1992, supra). Instrument-based pH testing during surgery determined that individual pharynx pH rarely varied by more than 1.0 pH unit in the absence of regurgitation (Joshi, G., et al., "Continuous hypopharyngeal pH measurement in spontaneously breathing anesthetized outpatients: laryngeal mask airway versus tracheal intubation," *Anesth. Analg.*, 1996; 82: 254–7). No previous studies have considered the gargling method for detecting acid reflux. Furthermore, no prior medical literature or patents have described the collection of fluid from gargling and measurement of the pH of this fluid, within a collection container or device as a means of evaluating for presence of acid reflux.

Several patents disclose methods involving the placement of devices in the oral cavity to obtain an oral sample for testing. See, for example, U.S. Pat. No. 4,114,605, "Intraoral cup for collecting saliva and method of using the same" (McGhee et al.), U.S. Pat. No. 4,418,702, "Method and apparatus for collecting saliva" (Brown et al.), U.S. Pat. No. 5,103,386, "Oral collection device and kit for immunoassay" (Goldstein et al.), U.S. Pat. No. 5,339,829, "Oral collection device" (Thieme et al.), U.S. Pat. No. 5,479,937, "Oral collection device" (Thieme et al.), U.S. Pat. No. 5,563,073, "Personal blood alcohol level testing kit" (Titmas, T.) and U.S. Pat. No. 5,573,009, "Oral sample collection method" (Thieme et al.).

One published study discusses collecting the fluid from gargling for subsequent laboratory analysis of collected tissue cells for evidence of malignancy (Ayre, J., "The gargle test: new oral cancer screening method," *N.Y. State Dent. J.*, June-July 1972; 38(6): 345–50).

Other literature describes gargling to obtain a sample of fluid for subsequent laboratory identification of the types and quantities of microbial organisms present in the pharynx.

U.S. Pat. No. 4,321,251, "Detection of malignant lesions of the oral cavity utilizing toluidine blue rinse," (Mashberg, March, 1982) describes a method of rinsing and gargling with a specified solution to detect a color change within the mouth, for detection of malignant oral lesions.

U.S. Pat. No. 4,397,944, "Compositions for diagnosis of dental caries activity," (Komura, 8/83) describes a method of detecting the pH of dental plaque placed in a specified solution, using bromothymol blue or other coloring agents.

U.S. Pat. No. 5,022,409, "Oral rinse immunoglobulin collection kit for immunoassay and method thereof" (Goldstein et al.) discloses a method of rinsing the mouth to collect an oral sample for subsequent storage and transport for testing.

BRIEF SUMMARY OF THE INVENTION

No prior medical literature or patents describe methods or test kits involving the collection of an oral sample into a specified collection device wherein analysis of the collected fluid is directly performed, without manual sample manipulation, to provide a rapid result of the fluid characteristic of interest. Oral sampling refers to either rinsing or gargling with specified liquid. The process of rinsing involves taking water (or other fluid) in the mouth and swishing it about to cause it to come into contact with the mouth tissues. The methods of this invention are easily applied to fluid produced by rinsing and/or gargling with a specified liquid and retrieving the resulting fluid from the mouth or pharynx.

None of the existing art describe a process of rinsing or gargling followed by collection of the resulting fluid into a device for rapid analysis of the characteristic of interest, without need for professional assistance in sample collection or laboratory analysis. Hence, this invention may be applied to provide a means for point-of-care, or self-test detection of any condition of the human mouth and pharynx which can be directly and rapidly assessed from fluid collected by oral sampling (rinsing and/or gargling), without need for professional assistance for sample collection or manual sample manipulation. Numerous important health conditions affect the mouth or pharynx and therefore may be rapidly and easily detected by this method. The range of analyses which can be performed on fluid collected in this manner from the mouth or pharynx is limited merely by the availability of rapid, non-instrumented assays which can be incorporated into the collection device which directly receives the fluid following rinsing and/or gargling with specified liquid.

It is therefore an object of this invention to provide a non-invasive, non-instrumented method of sampling the human mouth and pharynx which overcomes the drawbacks of the prior art, through the process of rinsing the mouth or gargling with specified liquid; collection of the resulting fluid directly into a collection container or device without the need for professional assistance in sample collection and retrieval; and subsequent rapid or point-of-care assessment and diagnosis of a specified characteristic of the mouth or pharynx by analysis of the fluid in the collection container or device, without the need for laboratory procedures.

It is another object of this invention to apply the procedures of gargling and fluid collection and analysis for the assessment and diagnosis of the presence and degree of acid reflux, which overcomes the drawbacks and limitations of the prior art.

It is another object of this invention to provide a method for assessing the presence and extent of acid reflux which can be used safely and easily by laypersons at home, and also by medical professionals in clinical environments.

It is another object of this invention to provide a test kit for sampling the pharynx and for assessing the presence and extent of acid reflux.

It is a further object of this invention to provide a test kit for assessing the presence and extent of reflux which can be performed by laypersons as a home test, and by medical professionals.

The present invention fulfills all of these needs by employing the process of gargling to sample the pharynx and collection of the resulting fluid to rapidly determine the acidity or pH, the latter being affected by the presence of acid reflux. The process of gargling involves taking water (or other fluid) in the lower pharynx or throat and forcing expired breath through it while holding the head back, without intentional swallowing. The resulting fluid can then be retrieved by tilting the head forward and allowing the fluid to fall by force of gravity, through the open mouth directly into a collection device.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENTS

Figure 1:
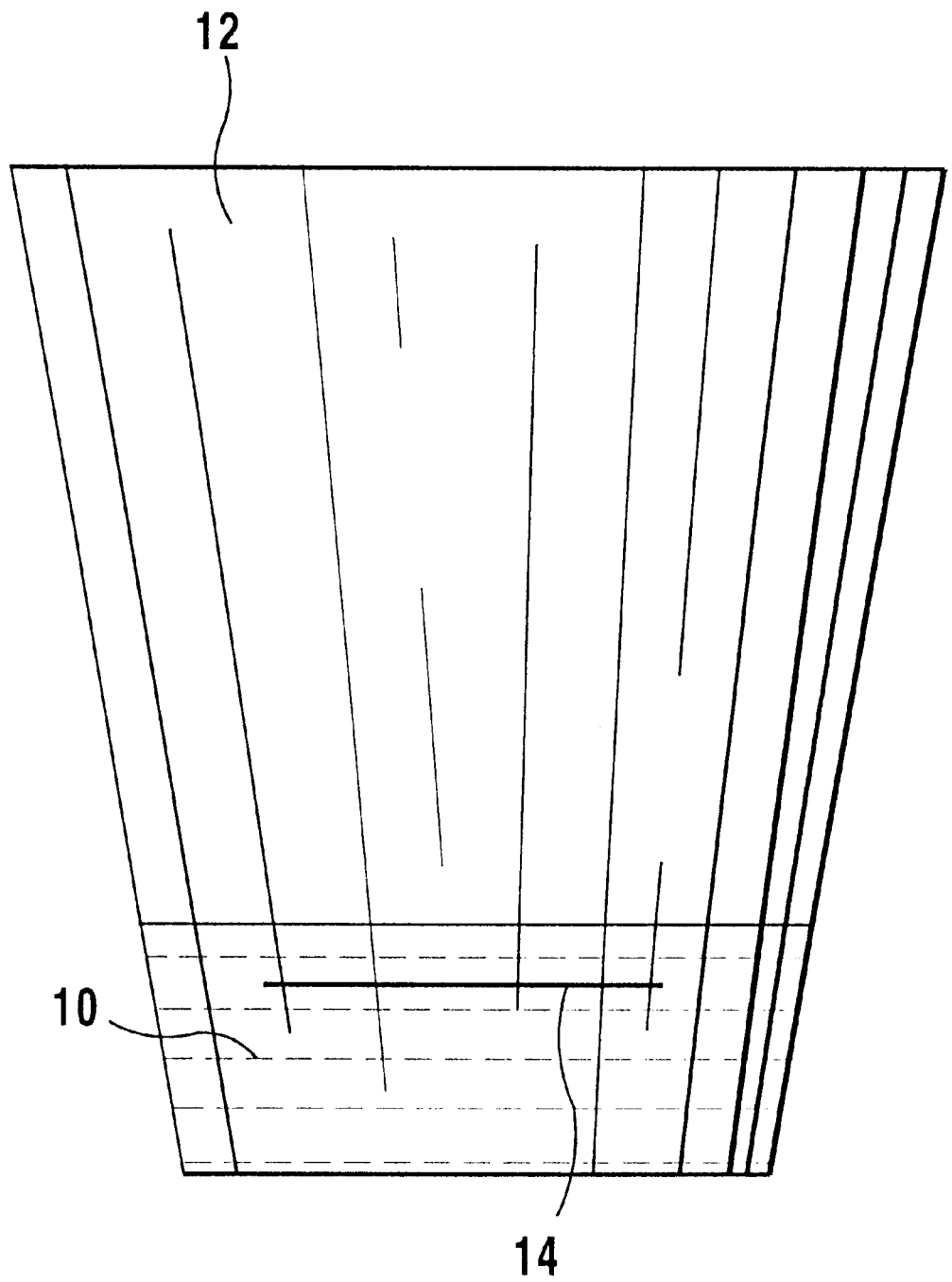
FIG. 1 illustrates the reusable container used to collect the gargle fluid (collection container) in the present invention.

Turning now descriptively to the drawings, in which similar reference characters denote similar elements throughout the several views, the Figures illustrate an oral sampling method and test kit of the present invention. With regard to the reference numerals used, the following numbering is used throughout the various drawing figures.

10 sampling liquid 12 container for collecting 10

14 horizontal indicator on 12

16 article for measuring 10 prior to use 18 bottle of bromothymol blue pH indicator solution 20 pH color chart 22 comparative pH color grid on 20

24 white area on 20 for facilitating color comparison 26 instruction manual for test kit 28 container for holding unused 10

In a preferred embodiment, the present invention includes a non-invasive, non-instrumented method and test kit for presence and extent of gastroesophageal or acid reflux, the condition whereby contents of the stomach travel retrograde up the esophagus and into the pharynx or throat area. The test involves obtaining fluid from the pharynx by the process of gargling with a specified liquid 10, followed by collection of the resulting fluid (hereinafter referred to as "gargle fluid") and measurement of the pH or level of acidity of the gargle fluid using calorimetric or other measurement techniques, and comparing the results to specified gargle fluid pH levels to identify presence and degree of acid reflux. The invention may be used both for purposes of self-testing in the home as well as by medical professionals in patient diagnosis.

The method of detection of acid reflux provided by the present invention is non-invasive. That is, the invention is concerned with detecting the condition of refluxing of stomach contents or acid reflux, where said acid reflux reaches the pharynx, by assessing the pH of the lower pharynx (throat) without the use of instruments placed within the pharynx or other need for manual sampling of the pharynx. Studies demonstrating the frequent effects of acid reflux on the pharynx support the concept that measuring pH of fluid derived from the pharynx can be the basis of a non-invasive assay or test for evaluating acid reflux conditions in persons of the general population.

A simple, accurate, non-invasive method for detecting acid reflux by measuring the pH in the pharynx area has important implications for both consumers and the medical profession. Furthermore, the methods of this invention allow for rapid assessment and frequent reassessment of the pH level in the pharynx, where repeating the test is as simple as collecting and assaying additional samples of gargle fluid. In contrast, the prior art of instrumented measurement does not provide a rapid result and requires prolonged invasive monitoring which cannot be easily repeated.

Specifically, the present invention involves sampling of the pharynx by the process of gargling with a specified liquid 10, thereby allowing the liquid to come in contact with tissues of the pharynx through gargling, followed by collection of the resulting fluid for pH measurement. The collected fluid is referred to as "gargle fluid" or "retrieved sampling liquid." No body cavity need be invaded to perform the method herein and no potentially hazardous substances or materials come in contact with the body tissues with the method.

To that end, the present invention provides a simple test where the person on whom the test is being performed, whether a self-testing consumer or a patient of a medical professional in a health care setting, himself delivers a specified liquid of designated volume through the open mouth and into the pharynx or back of the throat, the liquid being measured and transferred using a simple teaspoon or similar device 16. This is immediately followed by gargling with the liquid for a specified period to cause the liquid to now contact the lower pharynx. The resulting gargle fluid is then retrieved by opening the mouth, tilting the head forward and allowing the fluid to fall by force of gravity into the designated collection container 12, where the pH of the fluid in the container can then be easily assayed. Alternatively, the medical professional can perform the pH assay for the patient once the patient has collected the gargle fluid in the health care setting. The test can be carried out by any conscious individual capable of performing the gargling maneuver and can be performed by an adult without assistance, and under supervision of an adult in the case of an older child capable of performing the gargling maneuver.

By its nature, the gargling method samples the lower pharynx area as a whole, in contrast to prior art where an instrument probe is used to detect pH and is positioned at a single point in the pharynx. The liquid used for gargling, by coming into contact with the pharyngeal tissues has its original pH characteristic altered by the pH of the pharyngeal tissues. Similarly, the liquid used for gargling dilutes the acid status of the pharynx as it contacts the tissues, creating the gargle fluid which is then retrieved.

As it is derived from this mixing process between the liquid used for gargling and the pharynx, the gargle fluid method of pharynx pH detection reflects the contribution of the lower pharyngeal tissues as a whole as well as the liquid used for gargling, and therefore may yield a somewhat less acid pH as compared to pH measured by instrument probe. Ideally, the volume of liquid used for gargling should be such that the characteristic of interest of the pharynx is most effectively sampled. By this method, different volumes of liquid may potentially be used without digressing from the scope or spirit of this invention.

For measurement of gargle fluid pH in the collection container 12, different forms of commercially available pH test materials may be utilized. These are typically colorimetric methods, providing a visual color upon mixing or contact with the gargle fluid which is then matched with a corresponding color chart 20 to identify the pH of the gargle fluid. Different pH detection substances include phenaphthazine-impregnated paper, litmus powder and bromothymol blue solution 18. It has been found however, that paper and litmus powder materials have limited sensitivity to detect pH level changes in the particular ranges relevant to gargle fluid testing. Also, use of a pH detection solution such as bromothymol blue 18 is particularly suited to gargle fluid pH determination. It can be added in droplet form and thereby mixed directly with the gargle fluid within the collection container, providing a color to the gargle fluid upon mixing which can then be visualized through the clear container 12 and matched with the provided pH color chart 22 to determine gargle fluid pH.

The bromothymol blue pH test solution uses a color scale in gradations of 0.2 pH units (two-tenths of a pH unit difference per each specified color) with a total pH range of 6.0 to 7.6. This range has been found to be suitable for gargle fluid pH detection in normal as well as acid reflux periods. A pH detection system employing a smaller gradation scale, i.e., one-tenth (0.1) of a pH unit difference per each specified color could also be employed if such were available. Furthermore, a pH indicator system employing a range greater than 6.0 to 7.6 could be readily utilized. The pH of the collected gargle fluid could also be determined by non-colorimetric means such as digital electronic meter, if so desired. By this method, different systems may be implemented to determine the pH of gargle fluid within the collection container without digressing from the scope or spirit of this invention.

The present embodiment of the test for acid reflux defined herein includes (1) providing a liquid of known characteristics 10, including pH, to be used in gargling. If normal tap water is used as the liquid for gargling, the water source should be run until the water is clear and cold. Other liquids may be used for gargling, such as bottled water or saline solution. The method also includes (2) maintaining a minimum specified time interval between the test person's last ingestion of food or liquid, and/or mouth or dental hygiene procedures (a suitable minimum time interval generally being one-half hour or 30 minutes) and testing the pH of the collected gargle fluid. The purpose of this time interval is to ensure that residual amounts of ingested substances in the mouth or throat do not affect test results, by altering the pH of collected gargle fluid.

Preferably, the method includes another step (3) of first rinsing the mouth with any tap water (without gargling) and then expectorating to remove excess saliva and any debris present therein which could affect sample collection during the gargling process; (4) measuring out and placing a specified quantity, for example, one (1) teaspoon, or 5 ml, of the liquid used for gargling (e.g., from the tap water source or a bottled source) through the mouth and depositing it toward the back of throat; (5) followed by gargling for a period of at least 5 seconds, with the head titled back to maintain contact of the liquid against the throat or lower pharynx, and without swallowing; (6) collecting the resultant gargle fluid by tipping the head forward and allowing the gargle fluid to fall via gravity force through the open mouth, into the designated collection container without expectoration (that is, without spitting into container); (7) providing a visual marker 14 on the collection container to indicate that a volume of gargle fluid adequate for the test system has been retrieved and collected for testing; (8) placing the designated amount (droplet) of pH indicator solution in the container and periodically lightly agitating same to ensure mixing with the gargle fluid; and (9) observing the color of the gargle fluid through the light-transmitting container at a period of 10 minutes thereafter, the purpose of the period of 10 minutes being to ensure stable color end-point. The end-point color at 10 minutes is visually compared to the pH-color chart 20 to determine the pH of the gargle fluid. In the present embodiment the gargle fluid color is compared with a color-pH chart supplied with the pH indicator solution.

Ideally, such gargle fluid within a collection container may be rapidly analyzed to diagnose any number of conditions affecting the pharynx, specifically those for which the process of gargling effectively samples for the condition of interest, which can then be detected in the retrieved gargle fluid. In particular, this includes acid reflux reaching and altering the pH of the pharynx. Examples of other health conditions which can affect the pharynx and may be detectable by rapid analysis of gargle fluid include microbial organisms (e.g., bacteria and viruses) and potentially other markers of acid reflux or other abnormal physiologic conditions.

Furthermore, while gargling provides a method for sampling of the pharynx, the methods of the invention may equally be applied to sampling of the mouth, by the process of rinsing of the mouth with a specified liquid and subsequent collection of this fluid for rapid analysis. Collection and analysis of fluid from rinsing may be used to diagnose any number of conditions affecting the mouth, specifically those for which the process of rinsing effectively samples for the condition of interest. Finally, the process of gargling and rinsing may be combined in the same test to obtain an oral sample for rapid analysis, where appropriate. Also, while the present embodiment uses a 5 ml volume of liquid for gargling, the volume of liquid for gargling and/or rinsing may be adjusted as needed for the specific test requirements.

Referring now to the Figures, FIG. 1 illustrates an embodiment of the collection container 12 of the present invention, for collection of gargle fluid 10 for purposes of measurement of pH of the fluid within the container. The apparatus of FIG. 1 is particularly suited to self-collection of gargle fluid from the open mouth, visual confirmation of adequate gargle fluid sample volume, visual identification of fluid color following addition of liquid pH indicator, and reusability for repeat testing by merely rinsing out the container and allowing it to dry. The container 12 is made of solid, light-penetrating glass or plastic and is cup-shaped to be held in the hand during fluid collection and to lie on a flat surface for subsequent fluid analysis. The open end of the container is of a diameter of about 6 cm, of suitable size for collection of fluid from the open mouth as the container is held in proximity to the mouth. The closed end is of a diameter of about 3 cm, of suitable size to allow for the adequate gargle fluid sample volume (at least $\frac{1}{3}$ teaspoon) to be of reasonable height for placement of visual adequate volume indicator line 14, and also to allow the closed end to be stable when lying on a flat surface.

Figure 2:
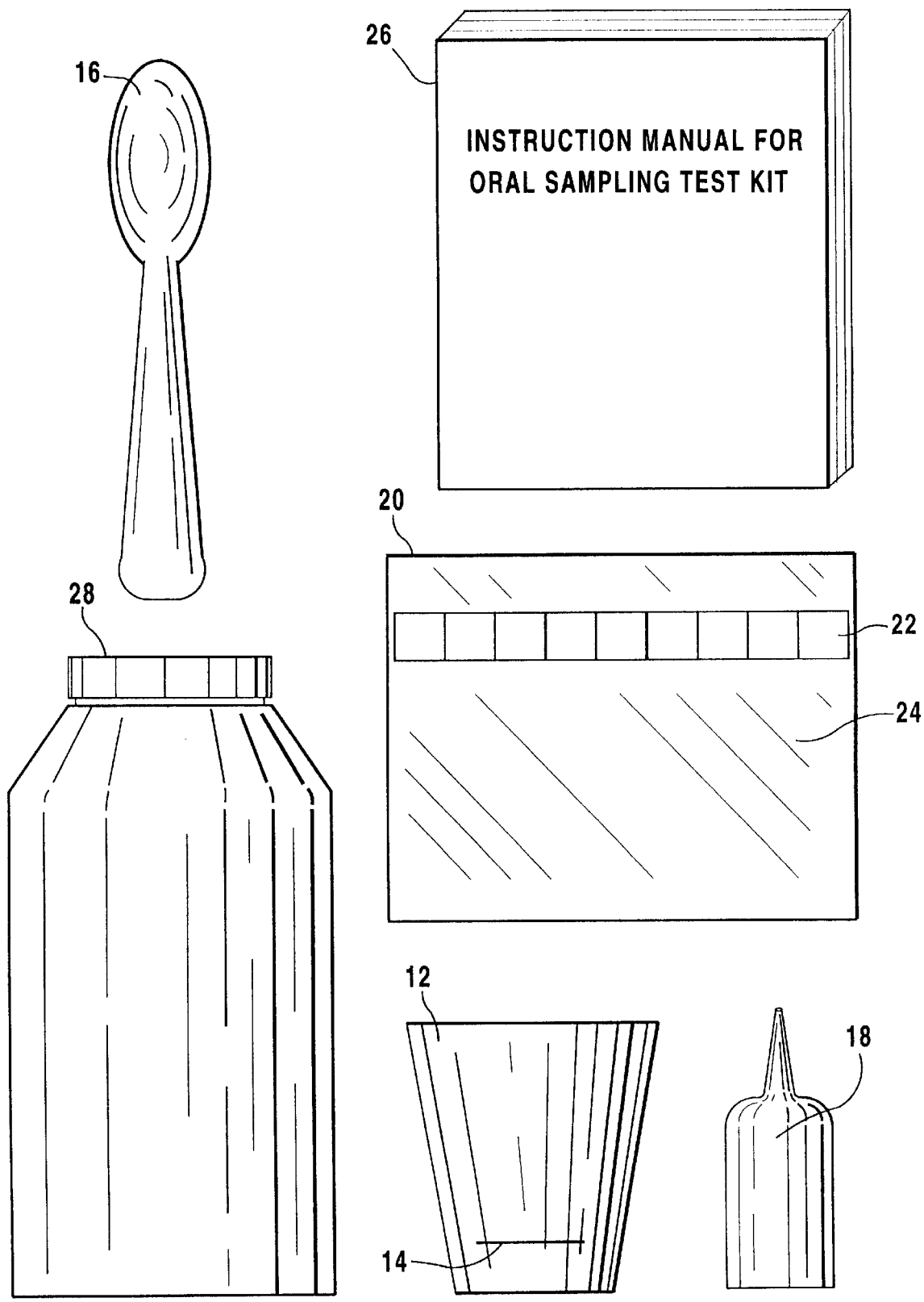
FIG. 2 illustrates the test kit of the present invention, including plastic reusable collection container, plastic reusable teaspoon, bottle of liquid for gargling (optional), dropper bottle of bromothymol blue pH detection solution and pH color chart with color-pH designations and a white area to be placed against collected fluid to assist in color identification.
Figure 1:
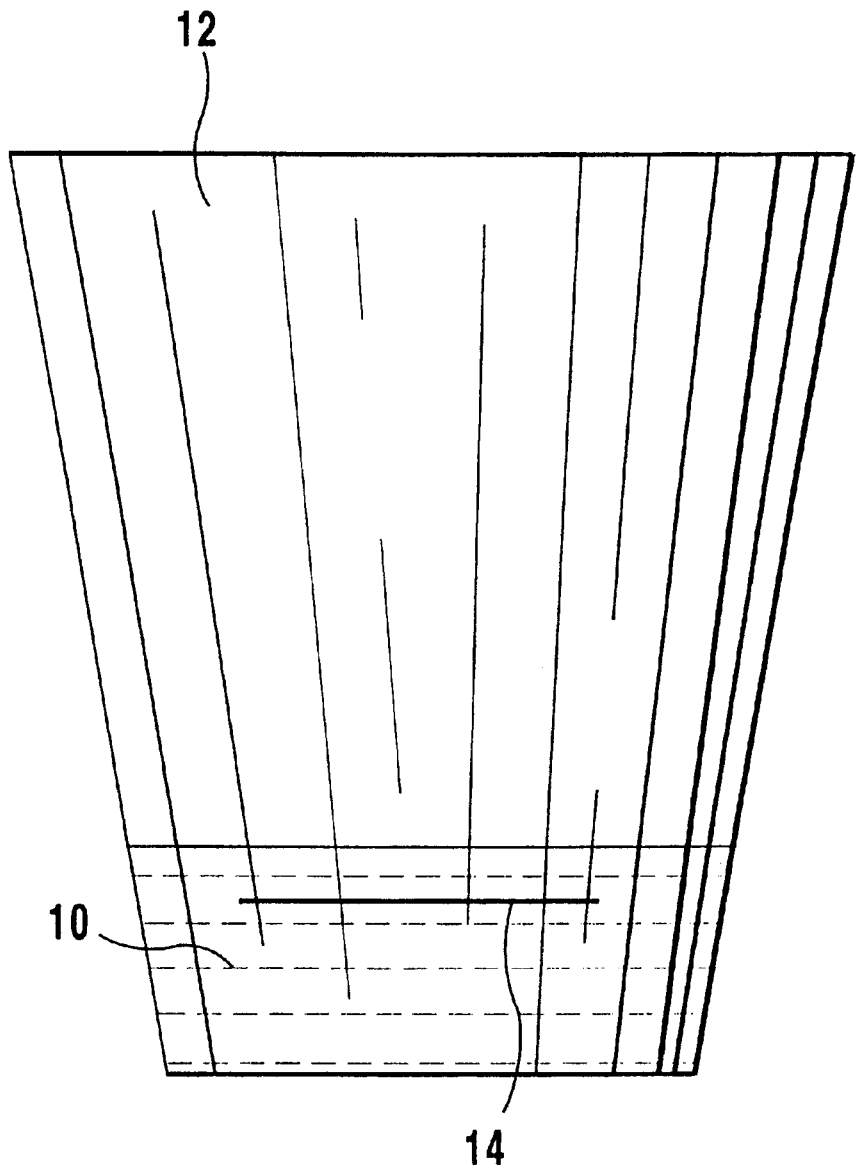
Figure 2:
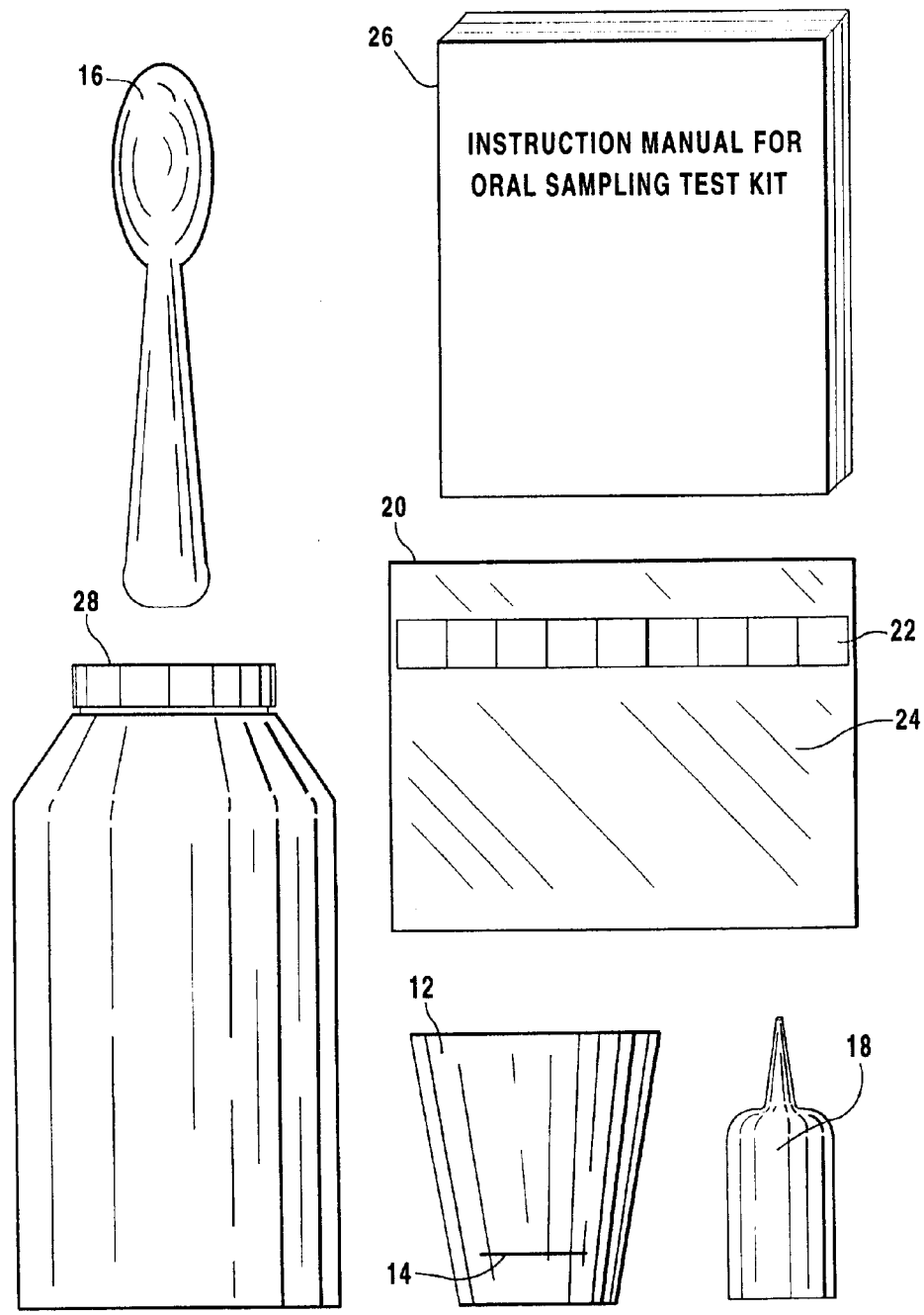

FIG. 2 illustrates an embodiment of the components of the test kit of the present invention, for collection and identification of gargle fluid pH for detection of the condition of acid reflux, as a reusable layperson's self-test or point-of-care test used by a medical professional in evaluation of a patient. The components of the test kit of FIG. 2 are particularly suited to self-collection of gargle fluid from the open mouth, addition of pH detection solution, visual identification of gargle fluid pH and frequent retesting. The resealable bottle of liquid 28 used for gargling contains a volume of specified liquid of known and stable characteristics, including pH, to allow for performance of multiple tests and portability of the test by ensuring a stable gargling liquid source. The bottle of gargling liquid is optional, as a stable source of tap water may be used as a source of liquid for gargling in the test. Plastic teaspoon 16 provides a means to measure out the designated amount of liquid for gargling and to place the liquid in the pharynx area. Resealable dropper bottle 18 contains a volume of pH indicator solution to allow for performance of multiple tests and is formed of plastic, whereby squeezing the container releases the pH indicator solution in individual droplet form. Chart 20 provides the color designations for the range of pH detected by the pH detection solution, with the color associated with each gradation of pH indicated in the respective box of area 22. Area 24 of chart 20 provides a white surface to aid in the matching of the gargle fluid color to the corresponding pH-color box of 22, by holding the collection container 12, containing the gargle fluid 10, against the white surface 24 following addition of the pH indicator solution 18.

EXAMPLES

A series of pH measurements was performed using the methods of the invention to evaluate pH analysis of gargle fluid as an indicator of acid reflux. Measurements were performed on gargle fluid samples collected from a subject with a history of intermittent acid reflux symptoms responsive to over-the-counter reflux treatments and/or dietary controls. Measurements were also performed to assess variability of gargle fluid pH between subjects and to confirm findings from the main subject testing. The process of rinsing without gargling, followed by collection and analysis of the fluid from rinsing was performed to evaluate the pH effects of saliva and to compare with gargling results. The testing demonstrated that gargle fluid pH was distinct from the pH of fluid collected by rinsing the mouth and testing this fluid (the latter referred to as "rinsing fluid") and that gargle fluid pH reflected acid reflux status. Different water sources for gargling were tested to assess variability and effect on pH measurements of the collected gargle fluid.

The materials used in the testing consisted of the following: (1) a cylindrical, cup-shaped container of translucent, solid material (plastic) for collection of gargle fluid, capable of being cleaned for reuse; (2) a source of liquid of known characteristics for gargling; (3) a plastic teaspoon for measurement of liquid for gargling; (4) bromothymol blue pH indicator solution, in a plastic bottle which released the solution in individual droplet form (for this test system, the mixing ratio of indicator solution to collected gargle fluid to yield a color change corresponding with gargle fluid pH, was 1 droplet for ⅓ to ⅔ teaspoon gargle fluid, the typical volume range of collected gargle fluid); (5) a pH color chart for the indicator solution, consisting of designations of color-pH associations and a white surface area to be held up against the gargle fluid in the collection container, to assist in identifying gargle fluid color and the corresponding pH.

The volume of 1 teaspoon (5 ml) was effective for gargling and resulted in a volume of gargle fluid sufficient for the pH test system. It is preferred that the starting volume of sampling liquid be from about 4 to about 10 ml, with a volume of 5 ml being particularly preferred. It was observed from the testing that gargling with 1 teaspoon of liquid (water) typically resulted in retrieval of about one-third (⅓) to two-thirds (⅔) teaspoon (about 2 to 4 ml) of gargle fluid in the collection container, when allowing the gargle fluid to fall by gravity into the container. On occasion, small amounts are swallowed during the gargling process without any harm, as the liquid is only water. When significant swallowing inadvertently occurs, this can affect the volume of gargle fluid collected.

Gargle fluid readily exits the mouth and enters the collection container upon opening the mouth and tilting the head forward so that the open mouth is above the container. After the bulk of the gargle fluid exits the mouth and enters the container, it is not necessary to continue collection. A portion of the liquid used for gargling is therefore normally retained in the pharynx and mouth following gargle fluid collection and can be expectorated into a sink. This retention does not present a problem for the testing, as a minimally sufficient amount of gargle fluid (about ⅓ teaspoon, or about 2 ml) can be easily and readily retrieved into the collection container for addition of the pH indicator solution and visualization of the color change. Furthermore, this collection method is preferable to attempting to retrieve a majority of the fluid by forceful ejection or expectoration, an action which may introduce contaminants such as saliva into the collected gargle fluid. The collection of ⅓ teaspoon or more gargle fluid was found to be adequate in this test system for addition of 1 droplet of bromothymol blue pH indicator solution and visualization of the resulting color change.

The measurement range of the pH indicator solution, pH 6.0 to pH 7.6, was found to be suitable for measurement of the range of gargle fluid pH levels associated with non-symptomatic and acid reflux periods. Testing demonstrated test subject gargle fluid pH to vary within the range of 6.2 to 7.6. A pH level of 6.2 was observed on some measurements performed immediately upon arising. The system allowed for visual determination of pH by color change in gradations of 0.2 pH units, suitable for assessing gargle fluid pH changes corresponding with acid reflux status. Baseline (non-symptomatic) daytime gargle fluid pH levels were found to differ somewhat within and between test subjects but were typically in the 7.0 to 7.6 range.

Gargle fluid pH levels associated with symptomatic acid reflux occurring after meals were typically below the subject's baseline (non-symptomatic) level by 0.4 or more pH units or below pH 7.0. Subject testing comparing non-symptomatic with symptomatic periods during evening post-meal times demonstrated gargle fluid pH to typically be in the range of 7.0 to 7.6 for non-symptomatic periods and below 7.0 range for symptomatic periods.

The testing showed that the pH of gargle fluid using the methods of the invention is distinct for a given sample and is reproducible. This reproducibility is observed with repeat testing performed at the same point in time; and with inter-day testing, demonstrating a diurnal pattern during non-symptomatic periods. Testing demonstrated that repeated measurements with a short period of time (15 minutes) between tests showed consistent results. The results of the testing showed that gargle fluid pH was often lowest in the morning and would rise somewhat during the day. Testing showed typical non-symptomatic AM gargle fluid pH to be around 7.0–7.2; typical non-symptomatic PM gargle fluid pH was in the range of 7.2–7.6.

The testing showed that pH measurements of gargle fluid are independent of the pH of ingested food or liquids or oral hygiene activities, when the test methods described are followed. Testing showed that using the methods as described, including a one-half hour waiting period between food/liquid ingestion or oral hygiene activities and gargle fluid collection, as well as rinsing the mouth and expectorating prior to gargling, valid gargle fluid pH measurements were obtained. The test method ensures that the results of gargle fluid pH are not affected by residual effects of the pH of ingested substances.

The testing showed that source and pH of the water used in performing the test can have a small effect on gargle fluid pH results. Fresh tap water is a suitable source of liquid for gargling. Same-source tap water was observed to have a generally stable pH when allowing the water to run until clear and cold. At times, same-source tap water could demonstrate a pH variation of greater than 1.0 pH unit, depending on the time of testing. Different tap water sources were observed to have a pH range extending to the endpoints of the pH test system, from 6.0 to 7.6. Repeat testing demonstrated that for a difference in pH of the liquid used for gargling of 1.0 or greater, there was no more than a 0.2 to 0.4 difference in gargle fluid pH.

The small differences in gargle fluid pH relative to the much larger differences in source water pH demonstrates that gargle fluid effectively samples the pH characteristic of the pharynx. The pH of the gargle fluid primarily results from the conditions of the pharynx and is only somewhat affected by the characteristics of the liquid used for gargling. Bottled water with stable characteristics, including pH is a suitable water source for gargling and allows for portability of the test by ensuring that water source pH factors do not have any effect on test results, such as when traveling or other instances where tap water sources may vary in their characteristics.

The testing demonstrated that the changes in the pH of the pharynx induced by acid reflux can be detected by the gargling method. pH measurements of gargle fluid were consistent with known characteristics of acid reflux as determined from prior studies, e.g., intermittent or episodic nature of acid reflux periods and beneficial effects of acid reflux treatments. The testing demonstrated that gargle fluid pH was predictably higher (less acid) during non-symptomatic periods and lower (more acid) during acid reflux periods and that the degree of gargle fluid acidity varied directly with the degree of symptoms.

Testing also demonstrated beneficial effects of acid reflux treatments, e.g., antacid/H2-receptor antagonists, showing an increase in gargle fluid pH (less acid) with accompanying decrease in symptoms, following use of liquid antacid or over-the-counter H2-receptor antagonist medication. These changes were typically in the range of 0.4 pH units or more and were associated with relief of acid reflux symptoms. Using the test methods described, a change (decrease) in pH of gargle fluid of around 0.4 units from baseline (non-symptomatic) periods corresponds with symptomatic acid reflux periods. A subsequent increase in pH of similar magnitude corresponded with effective treatment response or natural resolution of the acid reflux condition.

Using the test methods as described, pH measurements of gargle fluid are distinct from saliva, the latter being assessed by collection and analysis of rinsing fluid. The pH changes of gargle fluid induced by acid reflux treatments, e.g., H2-receptor antagonists are also distinct from potential treatment effects on saliva characteristics.

In summary, the testing demonstrated that pH measurements of gargle fluid, using the test methods described reflect acid reflux status. The ability of gargle fluid pH to identify acid reflux status results from the movement of refluxed stomach contents to the level of the pharynx and resulting effect on pharynx pH. The pH measurement of gargle fluid provides an effective non-invasive, non-instrumented method for assessment of the presence and extent of acid reflux. It involves no contact of hazardous substances with the body and can be performed by any individual capable of carrying out the test procedures as described. The test method is ideally suited as a home test. The ease of performance of pH measurement of gargle fluid provides an effective means to assess the presence and extent of acid reflux for the general population. The method also allows for frequent retesting.

While the invention has been illustrated and described as embodied in a method and test kit for oral sampling, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. A method for diagnosis of the condition of gastroesophageal reflux in a human, comprising:

(a) having said human gargle with a measured amount of a fully characterized sampling liquid, causing said sampling liquid to be in contact with the lower aspects of the pharynx of said human;

(b) retrieving said sampling liquid for analysis by having said human tilt the head down over a collection container, opening the mouth, and allowing said sampling liquid to exit the open mouth, via gravity, directly into the collection container; and (c) measuring the pH of the retrieved sampling liquid in said collection container and comparing said pH with specified pH values, to determine the presence and extent of gastroesophageal reflux in said human.

2. The method as defined in claim 1, wherein the step of gargling with said sampling liquid is for a period of at least 5 seconds.

3. The method as defined in claim 1, wherein said measuring of pH is performed by a technique selected from the group consisting of calorimetric indicator substance, pH meter and digital read device.

4. The method as defined in claim 1, wherein said pH is correlated to the presence and extent of gastroesophageal reflux, with said pH being a function of the presence and extent of gastroesophageal reflux.

5. The method as defined in claim 1, wherein said sampling liquid comprises about 5 ml potable water of known pH.

6. The method as defined in claim 5, wherein said water is selected from the group consisting of tap water, bottled water, distilled water or saline solution.

7. The method as defined in claim 1, wherein said collection container is of a shape and size suitable to be held in the hand and to allow for collection of said sampling liquid as it falls from the mouth by gravity force, said collection container being held under the mouth with the head tilted forward.

8. The method as defined in claim 1, wherein said retrieved sampling liquid has a volume of at least about 2 ml.

9. The method as defined in claim 3, wherein said pH is determined by combining with said retrieved sampling liquid an appropriate amount of a pH indicator selected from the group consisting of pH indicator solution, pH indicator powder and pH indicator paper.

10. The method as defined in claim 9, wherein:

(a) said pH indicator is bromothymol blue solution having a pH scale of about 6.0 to 7.6 pH units, with distinct color intervals of 0.2 pH units or less;

(b) said bromothymol blue solution is added dropwise to said retrieved sampling liquid followed by periodic light agitation of said collection container to ensure mixing of said bromothymol blue solution with said retrieved sampling liquid; and (c) the resulting color of said retrieved sampling liquid is observed after a suitable period of time from addition of said bromothymol blue solution, through said collection container, to determine the pH of said retrieved sampling liquid by comparison of said color with a pH-color chart provided with said bromothymol blue solution.

* * * * *

UNITED STATES PATENT AND TRADEMARK OFFICE
CERTIFICATE OF CORRECTION

PATENT NO. : 6,152,887 Page 1 of 12
DATED : November 28, 2000
INVENTOR(S) : Blume It is certified that error appears in the above-identified patent and that said Letters Patent is hereby corrected as shown below:

See Abstract.

See Specification.

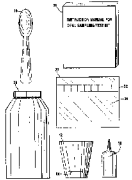

Signed and Sealed this

Twenty-seventh Day of August, 2002

Attest:

Attesting Officer

JAMES E. ROGAN
Director of the United States Patent and Trademark Office

United States Patent [19]
Blume

[11] Patent Number: 6,152,887
[45] Date of Patent: Nov. 28, 2000

[54] METHOD AND TEST KIT FOR ORAL SAMPLING AND DIAGNOSIS

[76] Inventor: Richard Stephen Blume, 240 Main St., Northport, N.Y. 11768

[21] Appl. No.: 09/031,578

[22] Filed: Feb. 27, 1998

[51] Int. Cl.$^7$ ................................................ A61B 5/00
[52] U.S. Cl. ...................................... 600/573; 604/317
[58] Field of Search ................................ 600/573, 576, 600/581; 604/317

[56] References Cited

U.S. PATENT DOCUMENTS

| | | |
|---|---|---|
| 4,114,605 | 9/1978 | McGhee et al. |
| 4,321,251 | 3/1982 | Mashberg |
| 4,397,944 | 8/1983 | Komura |
| 4,418,702 | 12/1983 | Brown et al. |
| 5,022,409 | 6/1991 | Goldstein et al. |
| 5,103,386 | 4/1992 | Goldstein et al. |
| 5,339,829 | 8/1994 | Thieme et al. |
| 5,479,937 | 1/1996 | Thieme et al. |
| 5,563,073 | 10/1996 | Titmas |
| 5,573,009 | 11/1996 | Thieme et al. |
| 5,786,227 | 7/1998 | Charlton ............................ 600/573 |

OTHER PUBLICATIONS

Singh, S. et al., "Determinants of esophageal 'alkaline' pH environment in controls and patients with gastroesophageal reflux disease," *Gut*, 1993 Mar.; 34(3): 309–16.
Chen, M., et al., "Gastroesphageal reflux disease: correlation of esophageal pH testing and radiographic findings," *Radiology*, 1992; 185: 483–6.
Kahrilas, P., "Gastroesophageal reflux disease," *JAMA*, Sep. 25, 1996; 276(12): 983–8.
Schoeman et al., "Mechanisms of gastroesophageal reflux in ambulant healthy human subjects," *Gastroenterology*, 1995 Jan.; 108(1): 83–91.
Richter, J., "Extraesophageal presentations of gastroesophageal reflux disease," *Semin. Gastrointest. Dis.*, 1997 Apr.; 8(2): 75–89.

Wall Street Journal, "When your heartburn starts to linger after the holidays," Dec. 29, 1997.
Wiener, G., et al., "Chronic hoarseness secondary to gastroesophageal reflux disease: documentation with 24–hour ambulatory pH monitoring," *Am. J. Gastroenterol.*, 1989; 84(12): 1503–8.
Contencin, P., and Narcy, P., "Gastroesophageal reflux in infants and children: A pharyngeal pH monitoring study," *Arch. Otolaryngol. Head Neck Surg.*, 1992 Oct.; 118: 1028–30.
Pope, C., "Acid–reflux disorders," *N. Engl. J. Med.*, Sep. 8, 1994; 331(10): 656–60.
Meurman, J., et al., "Oral and dental manifestations in gastroesophageal reflux disease," *Oral Surg. Oral Med. Oral Pathol.*, 1994 Nov.; 78(5): 583–9.
Schroeder, P., et al., "Dental erosion and acid reflux disease," *Ann. Intern. Med.*, Jun. 1, 1995; 122(11): 809–15.

(List continued on next page.)

*Primary Examiner*—Cary O'Connor
*Assistant Examiner*—Pamela S. Wingood

[57] ABSTRACT

A non-invasive, non-instrumented method for oral sampling and subsequent rapid or point-of-care sample analysis and diagnosis, including pH determination for detecting the presence and extent of gastroesophageal reflux. The test for acid reflux includes sampling of the pharynx by gargling with specified sampling liquid and then retrieving the resulting gargle fluid and measuring its pH. The invention may be used both for rapid self-testing in the home as well as for point-of-care diagnosis by health professionals. The method for obtaining an oral sample includes an article (16) for measuring the sampling liquid for gargling, a container (12) for depositing the retrieved sampling liquid (10), the gargle fluid after gargling, a horizontal line (14) provided thereon to serve as an indicator that an adequate volume of retrieved sampling liquid (10), was collected, and diagnostic tools (18, 20, 22, 24) for identification of a characteristic of interest, such as pH, of the retrieved sampling liquid (10) within the collection container (12) at the time of retrieval.

10 Claims, 2 Drawing Sheets

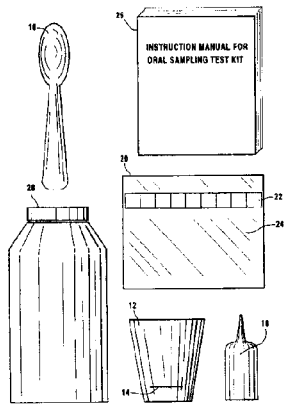

OTHER PUBLICATIONS

Madinier, I., et al., "Oral carriage of Helicobacter pylori: a review," *J. Periodontal.*, 1997 Jan.; 68(1):2–6.

Schindlbeck, N., et al., "Which pH threshold is best in esophageal pH monitoring?" *Am. J. Gastroenterol.*, 1991; 86(9): 1138–41.

Orr, W., et al., "The pattern of nocturnal and diurnal esophageal acid exposure in the pathogenesis of erosive mucosal damage," *Am. J. Gastroenterol.*, 1994 Apr.; 89(4): 509–12.

Jacob, P., et al., "Proximal esophageal pH–metry in patients with reflux laryngitis," *Gastroenterology*, 1991; 100: 305–10.

Shaker, R., et al., "Esophagopharyngeal distribution of refluxed gastric acid in patients with reflux laryngitis," *Gastroenterology*, 1995; 109: 1575–82.

Vaezi, M., and Richter, J., "Twenty-four hour ambulatory esophageal pH monitoring in the diagnosis of acid reflux–related chronic cough," *South Med. J.*, 1997 Mar.; 90(3): 305–11.

Koufman, J., and Cummins, M., "The prevalence and spectrum of reflux in laryngology: a prospective study of 132 consecutive patients with laryngeal and voice disorders," *Center for Voice Disorders of Wake Forest University*, 1997.

Locke, III, G., et al., "Prevalence and clinical spectrum of gastroesophageal reflux: A population–based study in Olmsted County, Minnesota," *Gastroenterology*, 1997; 112: 1448–56.

Isolauri, J., et al., "Natural course of gastroesophageal reflux disease: 17–22 year follow–up of 60 patients," *Am. J. Gastroenterol.*, 1997 Jan.; 92(1): 37–41.

Olden, K., and Triadafilopoulos, G., "Failure of initial 24–hour esophageal pH monitoring to predict refractoriness and intractability of reflux esophagitis," *Am. J. Gastroenterol.*, 1991; 86(9): 1142–6.

Jamieson, J., et al., "Ambulatory 24–hour esophageal pH monitoring: normal values, optimal thresholds, specificity, sensitivity, and reproducibility," *Am. J. Gastroenterol.*, 1992; 87(9): 1102–1110.

Tew, S., et al., "The illness behavior of patients with gastroesophageal reflux disease with and without endoscopic esophagitis," *Dis. Esophagus.*, 1997 Jan.; 10(1): 9–15.

Bardhan, K., "Is there any acid peptic disease that is refractory to proton pump inhibitors?" *Aliment. Pharmacol. Ther.*, 1993; 7 Suppl 1: 13–24.

Sachs, G., "Proton pump inhibitors and acid–related diseases," *Pharmacotherapy*, 1997 Jan.–Feb.; 17(1): 22–37.

Sontag, S., et al., "Lansoprazole heals erosive reflux esophagitis resistant to histamine H2–receptor antagonist therapy," *Am. J. Gastroenterol.*, 1997 Mar.; 92(3): 429–37.

Shaw, G., et al., "Subjective, laryngoscopic, and acoustic measurements of laryngeal reflux before and after treatment with omeprazole," *J. Voice.*, 1996 Dec.; 10(4): 410–8.

Devault, K. and Castell, D., "Guidelines for the diagnosis and treatment of gastroesophageal reflux disease," *Arch. Intern. Med.*, 1995; 155(20): 2165–2173.

Haase, G., et al., "A unique teletransmission sytem for extended four–channel esophageal pH monitoring in infants and children," *J. Ped. Surg.*, 1987 Jan.; 22(1): 68–74.

Contencin, P., et al., "Measurement of pH of the rhinopharynx in children with gastroesophageal reflux," *Presse Medicale*, 1989; 18(1): 13–6.

Joshi, G., et al., "Continuous hypopharyngeal pH measurement in spontaneously breathing anesthetized outpatients: laryngeal mask airway versus tracheal intubation," *Anesth. Analg.*, 1996; 82: 254–7.

Ayre, J., "The gargle test: new oral cancer screening method," *NY State Dent. J.*, 1972 Jun.–Jul.; 38(6): 345–50.

Loughlin, C., and and Koufman, J., "Paroxysmal laryngospasm secondary to gastroesophageal reflux," *Laryngoscope*, 1996 Dec.; 106(12 Pt. 1):1502–1505.

METHOD AND TEST KIT FOR ORAL SAMPLING AND DIAGNOSIS

BACKGROUND OF THE INVENTION

Field of the Invention

The present invention relates to health care diagnostics and specifically to a method for non-invasive, non-instrumented oral sampling in a human subject utilizing the collection of fluid from the pharynx of the subject. Fluid obtained from the pharynx (throat area) through gargling, is collected; analysis of the characteristic of interest in the fluid is performed in the specified collection container, providing a rapid result without manual handling of the fluid sample. More particularly, the present invention provides methods for non-invasive, non-instrumented assessment and diagnosis of the condition of acid reflux by sampling of the pharynx through the gargling process, and rapid determination of the pH of the collected fluid.

The use of diagnostic procedures or tests which provide rapid results in the health professional's office (point-of-care testing) have become an important component of medical practice. Such procedures are typically non- or minimally-invasive, require limited or no instrumentation and allow for efficient and cost-effective diagnosis. The development of rapid, non-invasive and non-instrumented technologies has increased the availability of consumer "home test" kits, allowing for layperson self-testing to identify important health conditions (e.g., pregnancy, blood in the stool, elevated cholesterol) and to promote appropriate and timely use of healthcare resources.

Gastroesophageal reflux (also referred to as "acid reflux") is the retrograde movement of acidic contents of the stomach into the esophagus and beyond. The body manages minor amounts of acid reflux, which are common in normal gastrointestinal function, by mechanical movement back toward the stomach in the normal direction of ingested food and liquid (known as peristalsis) and by neutralization by bicarbonate sources, including saliva (Singh, S. et al., "Determinants of esophageal 'alkaline' pH environment in controls and patients with gastroesophageal reflux disease," *Gut*, 1993 Mar; 34(3):309–16). As a result, the pH levels of tissues affected by minor amounts of acid reflux are maintained at normal levels. However, increased amounts of acid reflux overwhelm these corrective factors, resulting in greater acidity of affected tissues and the resulting symptoms of acid reflux. While the lining of the stomach is normally able to resist the adverse effects of stomach acid, this is not the case for tissues contacted by acid reflux including the esophagus and pharynx.

Acid reflux is considered to be the most common inflammatory disorder of the upper gastrointestinal tract (Chen, M. et al., "Gastroesophageal reflux disease: correlation of esophageal pH testing and radiographic findings," *Radiology*, 1992; 185:483–6) and is estimated to affect over 15 million Americans on a daily basis, and 40% of the population on a monthly basis (Kahrilas, P., "Gastroesophageal reflux disease," *JAMA*, 1996; 276(12):983–8 and American College of Gastroenterology, 1997). Acid reflux occurs most frequently within the first 3 hours after food intake (Schoeman, M. et al., "Mechanisms of gastroesophageal reflux in ambulant healthy human subjects," *Gastroenterology*, 1995; 108(1):83–91). Exposure of tissues to acid reflux results in symptoms including regurgitation, heartburn and sore throat and may lead to tissue damage. Symptoms and tissue damage caused by acid reflux are referred to in the medical profession as gastroesophageal reflux disease (GERD).

The occurrence of extraesophageal effects of acid reflux (effects outside the esophagus, i.e., in the pharynx or throat) due to acid reflux reaching to this area is increasingly being recognized in the medical community today (Chen et al, 1992, supra; Richter, J., "Extraesophageal presentations of gastroesophageal reflux disease," *Semin Gastrointest Dis.*, 1997; 8(2):75–89; and *Wall Street Journal*, "When your heartburn starts to linger after the holidays," Dec. 29, 1997). This causes various problems including hoarseness, laryngitis and chronic cough (Wiener, G. et al., "Chronic hoarseness secondary to gastroesophageal reflux disease: documentation with 24-hour ambulatory pH monitoring," *Am J Gastroenterol.*, 1989; 84(12):1503–8; Contencin, P., and Narcy, P., "Gastroesophageal reflux in infants and children: A pharyngeal pH monitoring study," *Arch Otolaryngol Head Neck Surg.*, 1992; 118:1028–30; Pope, C., "Acid-reflux disorders," *N Engl J Med.*, 1994; 331(10):656–60; and Kahrilas, 1996, supra). Because it may at times reach the mouth, acid reflux has been observed to have effects on this area as well (Meurman, J. et al., "Oral and dental manifestations in gastroesophageal reflux disease," *Oral Surg Oral Med Oral Pathol.*, 1994; 78(5):583–9; Schroeder, P. et al., "Dental erosion and acid reflux disease," *Ann Intern Med.*, 1995; 122(11):809–15; Madinier, I. et al., "Oral carriage of Helicobacter pylori: a review," *J Periodontol.*, 1997; 68(1):2–6).

Measurement of pH in the esophagus or pharynx using invasive instruments to detect refluxed acid (the sole method of pH measurement in acid reflux until the present invention) has determined that decreased pH (or greater acidity) is associated with refluxed acid and that decreased pH increases the risk of complications of acid reflux including esophageal erosion, laryngitis and chronic cough (Schindlbeck, N. et al., "Which pH threshold is best in esophageal pH monitoring?" *Am J Gastroenterol.*, 1991; 86(9):1138–41; Chen et al., 1992, supra; Orr, W. et al., "The pattern of nocturnal and diurnal esophageal acid exposure in the pathogenesis of erosive mucosal damage," *Am J Gastroenterol.*, 1994; 89(4):509–12; Jacob, P. et al., "Proximal esophageal pH-metry in patients with 'reflux laryngitis'," *Gastroenterology*, 1991; 100:305–10; Shaker, R. et al., "Esophagopharyngeal distribution of refluxed gastric acid in patients with reflux laryngitis" *Gastroenterology*, 1995; 109:1575–82; and Vaezi, M. and Richter, J., "Twenty-four hour ambulatory esophageal pH monitoring in the diagnosis of acid reflux-related chronic cough," *South Med J.*, 1997; 90(3): 305–11). Using instrument monitoring, 50 percent of adult ear-nose-throat patients were found to have abnormal amounts of refluxed acid reach to the level of the pharynx (Koufman, J., "The otolaryngologic manifestations of gastroesophageal reflux disease (GERD): a clinical investigation of 225 patients using ambulatory 24-hour pH monitoring and an experimental investigation of the role of acid and pepsin in the development of laryngeal injury," *Laryngoscope*, 1991; 101(4 Pt. 2 Suppl. 53):1–78).

The majority of persons with acid reflux symptoms do not seek professional medical evaluation and engage in self-treatment with widely-available over-the-counter medications (Locke III, G. et al., "Prevalence and clinical spectrum of gastroesophageal reflux: A population-based study in Olmsted County, Minnesota," *Gastroenterology*, 1997; 112:1448–56). These medications include antacids and drugs to reduce stomach acid production. However, while symptoms of acid reflux can be intermittent and may respond to over-the-counter medications, the condition often requires professional medical evaluation and treatment (Isolauri, J. et al., "Natural course of gastroesophageal reflux disease: 17–22 year follow-up of 60 patients," *Am J Gastroenterol.*, 1997; 92(1): 37–41). Perceived symptoms can be an unreliable indicator of the presence and extent of acid reflux (Olden, K., and Triadafilopoulos, G., "Failure of initial 24-hour esophageal pH monitoring to predict refractoriness and intractability of reflux esophagitis," *Am J Gastroenterol.*, 1991; 86(9):1142–6; Jamieson, J. et al., "Ambulatory 24-hour esophageal pH monitoring: normal values, optimal thresholds, specificity, sensitivity, and reproducibility," *Am J Gastroenterol.*, 1992; 87(9):1102–1110; and Tew, S. et al., "The illness behavior of patients with gastroesophageal reflux disease with and without endoscopic esophagitis," *Dis Esophagus.*, 1997; 10(1): 9–15). Without benefit of objective assessment, symptoms of acid reflux may be confused with other gastrointestinal conditions or other health problems which require professional medical evaluation, such as chest pain.

Effective acid reflux treatment requires accurate diagnosis. Many persons do not experience sufficient acid reduction with over-the-counter treatments and doses and therefore should receive medical evaluation and prescription medication (Bardhan, K., "Is there any acid peptic disease that is refractory to proton pump inhibitors?" *Aliment Pharmacol Ther.*, 1993; 7 Suppl. 1:13–24). The class of acid reflux prescription medications known as proton pump inhibitors can render superior results in treatment of acid reflux (Loughlin, C., and Koufman, J., "Paroxysmal laryngospasm secondary to gastroesophageal reflux," *Laryngoscope*, 1996; 106:1502–5; Kahrilas, 1996, supra; Sachs, G., "Proton pump inhibitors and acid-related diseases," *Pharmacotherapy*, 1997; 17(1):22–37; Sontag, S. et al., "Lansoprazole heals erosive reflux esophagitis resistant to histamine H2-receptor antagonist therapy," *Am J Gastroenterol.*, 1997; 92(3):429–37; and Koufman, J., and Cummins, M., "The prevalence and spectrum of reflux in laryngology: a prospective study of 132 consecutive patients with laryngeal and voice disorders," Center for Voice Disorders of Wake Forest University, 1997). Eighty-five percent of persons with laryngitis caused by acid reflux respond to omeprazole, a type of proton pump inhibitor (Shaw, G. et al., "Subjective, laryngoscopic, and acoustic measurements of laryngeal reflux before and after treatment with omeprazole," *J Voice*, 1996; 10(4):410–8). To ensure appropriate use of healthcare resources and effective treatment of acid reflux conditions, objective diagnosis is needed. Yet because of the limitations of current diagnostic methods, which involve invasive instruments, require prolonged testing and cannot be easily repeated, the large proportion of the general population which suffers with acid reflux is precluded from objective diagnostic evaluation (DeVault, K., and Castell, D., "Guidelines for the diagnosis and treatment of gastroesophageal reflux disease," *Arch Intern Med.*, 1995; 155(20): 2165–2173).

Previous methods have used invasive instruments to measure the pH of the pharynx area to detect refluxed acid. Instrument-based pH monitoring of points in the normal pharynx has shown results in a pH range of around 5 to 7.5 (Haase, G. et al., "A unique teletransmission system for extended four-channel esophageal pH monitoring in infants and children," *J Ped Surg.*, 1987; 22(1):68–74; Contencin, P. et al., "Measurement of pH of the rhinopharynx in children with gastroesophageal reflux," *Presse Medicale.*, 1989; 18(1):13–6; Wiener et al., 1989, supra; and Chen et al., 1992, supra). Instrument-based pH testing during surgery determined that individual pharynx pH rarely varied by more than 1.0 ph unit in the absence of regurgitation (Joshi, G. et al., "Continuous hypopharyngeal pH measurement in spontaneously breathing anesthetized outpatients: laryngeal mask airway versus tracheal intubation," *Anesth Analg.*, 1996; 82:254–7).

Several patents disclose methods involving the placement of devices in the oral cavity to obtain an oral sample for testing. See, for example, U.S. Pat. Nos. 4,114,605, "Intraoral cup for collecting saliva and method of using the same" (McGhee et al.), 4,418,702, "Method and apparatus for collecting saliva" (Brown et al.), 5,103,386, "Oral collection device and kit for immunoassay" (Goldstein et al.), 5,339,829, "Oral collection device" (Thieme et al.), 5,479,937, "Oral collection device" (Thieme et al.), 5,563,073, "Personal blood alcohol level testing kit" (Titmas, T.) and 5,573,009, "Oral sample collection method" (Thieme et al.).

One published study discusses collecting the fluid from gargling for subsequent laboratory analysis of collected tissue cells for evidence of malignancy (Ayre, J., "The gargle test: new oral cancer screening method," *NY State Dent J.*, 1972; 38(6):345–50).

Other literature describes gargling to obtain a sample of fluid for subsequent laboratory identification of the types and quantities of microbial organisms present in the pharynx.

U.S. Pat. No. 4,321,251, "Detection of malignant lesions of the oral cavity utilizing toluidine blue rinse," (Mashberg, March 1982) describes a method of rinsing and gargling with a specified solution to detect a color change within the mouth, for detection of malignant oral lesions.

U.S. Pat. No. 4,397,944, "Compositions for diagnosis of dental caries activity," (Komura, August 1983) describes a method of detecting the pH of dental plaque placed in a specified solution, using bromothymol blue or other colorimetric agent.

U.S. Pat. No. 5,022,409, "Oral rinse immunoglobulin collection kit for immunoassay and method thereof," (Goldstein et al.) discloses a method of rinsing the mouth to collect an oral sample for subsequent storage and transport for testing.

The problem with the prior art is that no prior medical literature or patents describe methods involving the collection of an oral sample by gargling into a specified collection device, wherein analysis of the collected fluid is directly performed, without manual sample manipulation, to provide a rapid result of the fluid characteristic of interest. More Particularly, none of the prior art provides for non-invasive detection of acid reflux by pH measurement.

SUMMARY OF THE INVENTION

This invention may be applied to provide a means for point-of-care, or self-test detection of a condition of the human pharynx which can be directly and rapidly assessed from fluid collected by oral sampling by gargling, without need for professional assistance for sample collection or manual sample manipulation. More particularly, the invention provides a method to non-invasively detect acid reflux by oral sampling. It is the surprising discovery of this invention that acid reflux can be detected without the need to detect refluxed acid, by determining the pH of tissues of the pharynx by fluid sampling, the tissue pH having been affected by occurrence of acid reflux.

It is therefore an object of this invention to provide a non-invasive, non-instrumented method of sampling the human pharynx which overcomes the drawbacks of the prior art, through the process of gargling with specified liquid; collection of the resulting fluid directly into a collection container or device without the need for professional assistance in sample collection and retrieval; and subsequent rapid or point-of-care assessment and diagnosis of a specified characteristic of the pharynx by analysis of the fluid in the collection container or device, without the need for laboratory procedures.

More particularly, it is an object of this invention to apply the procedures of gargling and fluid collection and analysis for the assessment and diagnosis of the presence and extent of acid reflux, which overcomes the drawbacks and limitations of the prior art by not requiring instrumented detection of refluxed acid.

It is another object of this invention to provide a method for assessing the presence and extent of acid reflux which can be used safely and easily by laypersons at home, and by medical professionals in clinical environments.

The present invention fulfills all of these needs by employing the process of gargling to sample the pharynx and collection of the resulting fluid to rapidly determine the acidity or pH, the latter being affected by the occurrence of acid reflux. The process of gargling involves taking water (or other sampling liquid) in the lower pharynx or throat and forcing expired breath through it while holding the head back, without intentional swallowing. The resulting fluid can then be retrieved by tilting the head forward and allowing the fluid to fall by force of gravity, through the open mouth directly into a collection container.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 illustrates the reusable collection container used to collect the gargle fluid in the present invention.

FIG. 2 illustrates materials for the method of the present invention, including plastic reusable collection container, plastic reusable teaspoon, bottle of sampling liquid for gargling (optional), dropper bottle of bromothymol blue pH detection solution and pH color chart with color-pH designations and a white area to be placed against collected fluid to assist in color identification.

DETAILED DESCRIPTION OF THE PREFERRED EMBODIMENTS

Turning now descriptively to the drawings, in which similar reference characters denote similar elements throughout the several views, the Figures illustrate the materials for an oral sampling method of the present invention. With regard to the reference numerals used, the following numbering is used throughout the various drawing figures.

10 retrieved sampling liquid
12 container for collecting 10
14 horizontal indicator on 12
16 article for measuring sampling liquid prior to use
18 bottle of bromothymol blue pH indicator solution
20 pH color chart
22 comparative pH color grid on 20
24 white area on 20 for facilitating color comparison
26 instruction manual
28 container holding unused sampling liquid In a preferred embodiment, the present invention includes a non-invasive, non-instrumented method for determining the presence and extent of gastroesophageal or acid reflux, the condition whereby contents of the stomach travel retrograde up the esophagus affecting the pharynx or throat area. The test involves obtaining fluid from the pharynx by the process of gargling with a specified sampling liquid, followed by collection of the retrieved sampling liquid 10 (hereinafter referred to as "gargle fluid") and measurement of the pH or level of acidity of the gargle fluid using colorimetric or other measurement techniques, and comparing the results to specified gargle fluid pH levels to identify presence and degree of acid reflux. The invention may be used both for purposes of self-testing in the home as well as by medical professionals in patient diagnosis.

The method of detection of acid reflux provided by the present invention is non-invasive. That is, the invention is concerned with detecting the condition of refluxing of stomach contents or acid reflux, where said acid reflux affects the tissues of the pharynx, by assessing the pH of the lower pharynx (throat) without the use of instruments placed within the pharynx or other need for manual sampling of the pharynx.

Specifically, the present invention involves sampling of the pharynx by the process of gargling with a specified sampling liquid, thereby allowing the liquid to come in contact with tissues of the pharynx through gargling, followed by collection of the resulting gargle fluid for pH measurement. No body cavity need be invaded to perform the method herein and no potentially hazardous substances or materials come in contact with the body tissues with the method.

The person on whom the test is being performed, whether a self-testing consumer or a patient of a medical professional in a healthcare setting, himself or herself delivers a specified sampling liquid of designated volume through the open mouth and into the pharynx or back of the throat, the liquid being measured and transferred using the same simple teaspoon or similar device 16. This is immediately followed by gargling with the sampling liquid for a specified period to cause the liquid to now contact the lower pharynx. The resulting gargle fluid is then retrieved by opening the mouth, tilting the head forward and allowing the fluid to fall by force of gravity into the designated collection container 12, where the pH of the fluid in the container can then be easily assayed by the person. Alternatively, the medical professional can perform the pH assay for the patient once the patient has collected the gargle fluid in the health care setting. The test can be carried out by any conscious individual capable of performing the gargling maneuver and can be performed by an adult without assistance, and under supervision of an adult in the case of an older child capable of performing the gargling maneuver.

By its nature, the gargling method samples the lower pharynx area as a whole, in contrast to prior art where a pH instrument probe is used to detect refluxed acid and is positioned at a single point in the pharynx. The liquid used for gargling, by coming into contact with the pharyngeal tissues has its original pH characteristic altered by the pH of the pharyngeal tissues. Similarly, the liquid used for gargling dilutes the acid status of the pharynx as it contacts the tissues, creating the gargle fluid which is then retrieved.

As it is derived from this mixing process between the liquid used for gargling and the pharynx, the gargle fluid method of pharynx pH detection reflects the contribution of the lower pharyngeal tissues as a whole as well as the liquid used for gargling, and therefore may yield a somewhat less acid pH as compared to pH measured by instrument probe. Ideally, the volume of liquid used for gargling should be such that the characteristic of interest of the pharynx is most effectively sampled. By this method, different volumes of liquid may potentially be used without digressing from the scope or spirit of this invention.

For measurement of gargle fluid pH in the collection container 12, different forms of commercially available pH test materials may be utilized. These are typically colorimetric methods, providing a visual color upon mixing or contact with the gargle fluid which is then matched with a corresponding color chart 20 to identify the pH of the gargle fluid. Different pH detection substances include phenaphthazine-impregnated paper, litmus powder and bromothymol blue solution 18. It has been found however, that paper and litmus powder materials have limited sensitivity to detect pH level changes in the particular ranges relevant to gargle fluid testing. Also, use of pH detection solution such as bromothymol blue 18 is particulary suited to gargle fluid pH determination. It can be added in droplet form and thereby mixed directly with the gargle fluid within the collection container, providing a color to the gargle fluid upon mixing which can then be visualized through the clear container 12 and matched with the provided pH color chart 22 to determine gargle fluid pH.

The bromothymol blue pH test solution uses a color scale in gradations of 0.2 pH units (two-tenths of a pH unit difference per each specified color) with a total pH range of 6.0 to 7.6. This range has been found to be suitable for gargle fluid pH detection in normal as well as acid reflux periods. A pH detection system employing a smaller gradation scale, i.e., one-tenth (0.1) of a pH unit difference per each specified color could also be employed if such was available. Furthermore, a pH indicator system employing a range greater than 6.0 to 7.6 could be readily utilized. The pH of the collected gargle fluid could also be determined by non-colorimetric means such as digital electronic meter, if so desired. By this method, different systems may be implemented to determine the pH of gargle fluid within the collection container without digressing from the scope or spirit of this invention.

The present embodiment of the test for acid reflux defined herein includes (1) providing a sampling liquid of known characteristics, including pH, to be used in gargling. If normal tap water is used as the liquid for gargling, the water source should be run until the water is clear and cold. Other liquids may be used for gargling, such as bottled water or saline. The method also includes (2) maintaining a minimum specified time interval between the test person's last ingestion of food or liquid, and/or mouth or dental hygiene procedures (a suitable minimum time interval generally being one-half hour or 30 minutes) and testing the pH of the collected gargle fluid. The purpose of this time interval is to ensure that residual amounts of ingested substances in the mouth or throat do not affect test results, by altering the pH of collected gargle fluid.

Preferably, the method includes another step (3) of first rinsing the mouth with any tap water (without gargling) and then expectorating to remove excess saliva and any debris present therein which could affect sample collection during the gargling process; (4) measuring out and placing one (1) teaspoon, or 5 ml. of the sampling liquid used for gargling (e.g., from the tap water source or a bottled source) through the mouth and depositing it toward the back of throat; (5) followed by gargling for a period of at least 5 seconds, with the head titled back to maintain contact of the liquid against the throat or lower pharynx, and without swallowing; (6) collecting the resultant gargle fluid by tipping the head forward and allowing the gargle fluid to fall via gravity force through the open mouth, into the designated collection container without expectoration (that is, without spitting into container); (7) providing a visual marker 14 on the collection container to indicate that a volume of gargle fluid adequate for the test system has been retrieved and collected for testing; (8) placing the designated amount (droplet) of pH indicator solution in the container and periodically lightly agitating same to ensure mixing with the gargle fluid; and (9) observing the color of the gargle fluid through the light-transmitting container at a period of 10 minutes thereafter, the purpose of the period of 10 minutes being to ensure stable color end-point. The end-point color at 10 minutes is visually compared to the pH-color chart 20 to determine the pH of the gargle fluid. In the present embodiment the gargle fluid color is compared with a color-pH chart supplied with the pH indicator solution.

Ideally, such gargle fluid within a collection container may be rapidly analyzed to diagnose any number of conditions affecting the pharynx, specifically those for which the process of gargling effectively samples for the condition of interest, which can then be detected in the gargle fluid. In particular, this includes acid reflux reaching and altering the pH of the pharynx. Examples of other health conditions which can affect the pharynx and may be detectable by rapid analysis of gargle fluid within the collection container include microbial organisms (e.g., bacteria and viruses) and potentially other markers of acid reflux or other abnormal physiologic conditions. The volume of liquid for gargling may be adjusted as needed for the specific test requirements.

Referring now to the Figures, FIG. 1 illustrates an embodiment of the collection container 12 of the present invention, for collection of retrieved sampling liquid 10, the gargle fluid for purposes of measurement of pH of the fluid within the container. The apparatus of FIG. 1 is particularly suited to self-collection of gargle fluid from the open mouth, visual confirmation of adequate gargle fluid sample volume, visual identification of fluid color following addition of liquid pH indicator, and reusability for repeat testing by merely rinsing out the container and allowing it to dry. The container 12 is made of solid, light-penetrating glass or plastic and is cup-shaped to be held in the hand during fluid collection and to lie on a flat surface for subsequent fluid analysis. The open end of the container is of a diameter of about 6 cm, of suitable size for collection of fluid from the open mouth as the container is held in proximity to the mouth. The closed end is of a diameter of about 3 cm, of suitable size to allow for the adequate gargle fluid sample volume (at least ⅓ teaspoon) to be of reasonable height for placement of visual adequate volume indicator line 2, and also to allow the closed end to be stable when lying on a flat surface.

FIG. 2 illustrates an embodiment of the components of the materials of the method of the present invention, for collection and identification of gargle fluid pH for detection of the condition of acid reflux. The materials of FIG. 2 are particularly suited to self-collection of gargle fluid from the open mouth, addition of pH detection solution, visual identification of gargle fluid pH and frequent re-testing. The resealable container of sampling liquid 28 used for gargling contains a volume of specified liquid of known and stable characteristics, including pH, to allow for performance of multiple tests and portability of the test by ensuring a stable sampling liquid source. The container of sampling liquid 28 is optional, as a stable source of tap water may be used as a source of liquid for gargling in the test. Plastic teaspoon 16 provides a means to measure out the designated amount of liquid for gargling and to place the liquid in the pharynx area. Resealable Dropper bottle 18 contains a volume of pH indicator solution to allow for performance of multiple tests and is formed of plastic, whereby squeezing the container releases the pH indicator solution in individual droplet form. Chart 20 provides the color designations for the range of pH detected by the pH detection solution, with the color associated with each gradation of pH indicated in the respective box of area 22. Area 24 of chart 20 provides a white surface to aid in the matching of the gargle fluid color to the corresponding pH-color box of 22, by holding the collection container 12, containing the retrieved sampling liquid 10, the gargle fluid against the white surface 24 following addition of the pH indicator solution 18.

EXAMPLES

A series of pH measurements was performed using the methods of the invention to evaluate pH analysis of gargle fluid as an indicator of acid reflux. Measurements were performed on gargle fluid samples collected from a subject with a history of intermittent acid reflux symptoms responsive to over-the-counter reflux treatments and/or dietary controls. Measurements were also performed to assess variability of gargle fluid pH between subjects and to confirm findings from the main subject testing. The process of rinsing without gargling, followed by collection and analysis of the fluid from rinsing was performed to evaluate the pH effects of saliva and to compare with gargling results. The testing demonstrated that gargle fluid pH was distinct from the pH of fluid collected by rinsing the mouth and testing this fluid (the latter referred to as "rinsing fluid") and that gargle fluid pH reflected acid reflux status. Different water sources for gargling were tested to assess variability and effect on pH measurements of the collected gargle fluid.

The materials used in the testing consisted of the following: (1) a cylindrical, cup-shaped container of translucent, solid material (plastic) for collection of gargle fluid, capable of being cleaned for reuse; (2) a source of liquid of known characteristics for gargling; (3) a plastic teaspoon for measurement of liquid for gargling; (4) bromothymol blue pH indicator solution, in a plastic bottle which released the solution in individual droplet form (for this test system, the mixing ratio of indicator solution to collected gargle fluid to yield a color change corresponding with gargle fluid pH, was 1 droplet for ⅓ to ⅔ teaspoon gargle fluid, the typical volume range of collected gargle fluid); (5) a pH color chart for the indicator solution, consisting of designations of color-pH associations and a white surface area to be held up against the gargle fluid in the collection container, to assist in identifying gargle fluid color and the corresponding pH.

The volume of 1 teaspoon (5 ml) was effective for gargling and resulted in a volume of gargle fluid sufficient for the pH test system. It was preferred that the starting volume of smapling liquid be from about 4 to about 10 ml, with a volume of 5 ml being particularly preferred. It was observed from the testing that gargling with 1 teaspoon of liquid (water) typically resulted in retrieval of about one-third (⅓) to two-thirds (⅔) teaspoon (about 2 to 4 ml) of gargle fluid in the collection container, when allowing the gargle fluid to fall by gravity into the container. On occasion, small amounts are swallowed during the gargling process without any harm, as the sampling liquid is only water. When significant swallowing inadvertently occurs, this can affect the volume of gargle fluid collected.

Gargle fluid readily exits the mouth and enters the collection container upon opening the mouth and tilting the head forward so that the open mouth is above the container. After the bulk of the gargle fluid exits the mouth and enters the container, it is not necessary to continue collection. A portion of the liquid used for gargling is therefore normally retained in the pharynx and mouth following gargle fluid collection and can be expectorated into a sink. This retention does not present a problem for the testing, as a minimally sufficient amount of gargle fluid (about ⅓ teaspoon, or about 2 ml) can be easily and readily retrieved into the collection container for addition of the pH indicator solution and visualization of the color change. Furthermore, this collection method is preferable to attempting to retrieve a majority of the fluid by forceful ejection or expectoration, an action which may introduce contaminants such as saliva into the collected gargle fluid. The collection of ⅓ teaspoon or more gargle fluid was found to be adequate in this test system for addition of 1 droplet of bromothymol blue pH indicator solution and visualization of the resulting color change.

The measurement range of the pH indicator solution, pH 6.0 to pH 7.6, was found to be suitable for measurement of the range of gargle fluid pH levels associated with non-symptomatic and acid reflux periods. Testing demonstrated test subject gargle fluid pH to vary within the range of 6.2 to 7.6, depending upon the presence and extent of acid reflux symptoms. A pH level of 6.2 was observed on some measurements performed immediately upon arising. The system allowed for visual determination of pH by color change in gradations of 0.2 pH units, suitable for assessing gargle fluid pH changes corresponding with acid reflux status. Baseline (non-symptomatic) daytime gargle fluid pH levels were found to differ somewhat within and between test subjects but were typically in the 7.0 to 7.6 range.

Gargle fluid pH levels associated with symptomatic acid reflux occurring after meals were typically below the subject's baseline (non-symptomatic) level by 0.4 or more pH units or below pH 7.0. Subject testing comparing non-symptomatic with symptomatic periods during evening post-meal times demonstrated gargle fluid pH to typically be in the range of 7.0 to 7.6 for non-symptomatic periods and below 7.0 range for symptomatic periods.

The testing showed that the pH of gargle fluid using the methods of the invention is distinct for a given sample and is reproducible. This reproducibility is observed with repeat testing performed at the same point in time; and with inter-day testing, demonstrating a diurnal pattern during non-symptomatic periods. Testing demonstrated that repeated measurements with a short period of time (15 minutes) between tests showed consistent results. The results of the testing showed that gargle fluid pH in non-symptomatic periods was often lowest in the morning and would rise somewhat during the day. Testing showed typical non-symptomatic AM gargle fluid pH to be around 7.0–7.2; typical non-symptomatic PM gargle fluid pH was in the range of 7.2–7.6.

The testing showed that pH measurements of gargle fluid are independent of the pH of ingested food or liquids or oral hygiene activities, when the test methods described are followed. Testing showed that using the methods as described, including a one-half hour waiting period between food/liquid ingestion or oral hygiene activities and gargle fluid collection, as well as rinsing the mouth and expectorating prior to gargling, valid gargle fluid pH measurements were obtained. The test method ensures that the results of gargle fluid pH are not affected by residual effects of the pH of ingested substances.

The testing showed that source and pH of the water used in performing the test can have a small effect on gargle fluid pH results. Fresh tap water is a suitable source of liquid for gargling. Same-source tap water was observed to have a generally stable pH when allowing the water to run until clear and cold. At times, same-source tap water could demonstrate a pH variation of greater than 1.0 pH unit, depending on the time of testing. Different tap water sources were observed to have a pH range extending to the endpoints of the pH test system, from 6.0 to 7.6. Repeat testing demonstrated that for a difference in pH of the water sampling liquid used for gargling of 1.0 or greater, there was no more than a 0.2 to 0.4 difference in gargle fluid pH.

The small differences in gargle fluid pH relative to the much larger differences in source water pH demonstrates that gargle fluid effectively samples the pH characteristic of the pharynx. The pH of the gargle fluid primarily results from the conditions of the pharynx and is only somewhat affected by the characteristics of the water sampling liquid used for gargling. Bottled water with stable characteristics, including pH is a suitable water source for gargling and allows for portability of the test by ensuring that water source pH factors do not have any effect on test results, such as when traveling or other instances where tap water sources may vary in their characteristics.

The testing demonstrated that the changes in the pH of the pharynx induced by acid reflux can be detected by the gargling method. pH measurements of gargle fluid were consistent with known characteristics of acid reflux as determined from prior studies, e.g., intermittent or episodic nature of acid reflux periods and beneficial effects of acid reflux treatments. The testing demonstrated that gargle fluid pH was predictably higher (less acid) during non-symptomatic periods and lower (more acid) during acid reflux periods and that the degree of gargle fluid acidity varied directly with the degree of acid reflux symptoms.

Testing also demonstrated beneficial effects of acid reflux treatments, e.g., antacid/H2-receptor antagonists, showing an increase in gargle fluid pH (less acid) with accompanying decrease in symptoms, following use of liquid antacid or over-the-counter H2-receptor antagonist medication. These changes were typically in the range of 0.4 pH units or more and were associated with relief of acid reflux symptoms. Using the test methods described, a change (decrease) in pH of gargle fluid of around 0.4 units from baseline (non-symptomatic) periods corresponds with symptomatic acid reflux periods. A subsequent increase in pH of similar magnitude corresponded with effective treatment response or natural resolution of the acid reflux condition.

Using the test methods as described, pH measurements of gargle fluid are distinct from saliva, the latter being assessed by collection and analysis of rinsing fluid. pH changes of gargle fluid induced by acid reflux treatments, e.g., H2-receptor antagonists are also distinct from potential treatment effects on saliva characteristics.

In summary, the testing demonstrated that pH measurements of gargle fluid, using the test methods described reflect acid reflux status. The ability of gargle fluid pH to identify acid reflux status results from the retrograde movement of refluxed stomach contents to affect the pH of the tissues of the pharynx. The pH measurement of gargle fluid provides an effective non-invasive, non-instrumented method for assessment of the presence and extent of acid reflux. It involves no contact of hazardous substances with the body and can be performed by any individual capable of carrying out the test procedures as described. The test method is ideally suited as a home test. The ease of performance of pH measurement of gargle fluid provides an effective means to assess the presence and extent of acid reflux for the general population. The method also allows for frequent retesting.

While the invention has been illustrated and described as embodied in a method for oral sampling, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by letters patent is set forth in the appended claims:

1. A method for diagnosis of the condition of gastroesophageal reflux in a human, comprising:
    (a) having said human gargle with a measured amount of a fully characterized sampling liquid, causing said sampling liquid to be in contact with the lower aspects of the pharynx of said human;
    (b) retrieving said sampling liquid for analysis by having said human tilt the head down over a collection container, opening the mouth, and allowing said sampling liquid to exit the open mouth, via gravity, directly into the collection container; and
    (c) measuring the pH of the retrieved sampling liquid in said collection container and comparing said pH with specified pH values, to determine the presence and extent of gastroesophageal reflux in said human.

2. The method as defined in claim 1, wherein the step of gargling with said sampling liquid is for a period of at least 5 seconds.

3. The method as defined in claim 1, wherein said measuring of pH is performed by a technique selected from the group consisting of calorimetric indicator substance, pH meter and digital read device.

4. The method as defined in claim 1, wherein said pH is correlated to the presence and extent of gastroesophageal reflux, with said pH being a function of the presence and extent of gastroesophageal reflux.

5. The method as defined in claim 1, wherein said sampling liquid comprises about 5 ml potable water of known pH.

6. The method as defined in claim 5, wherein said water is selected from the group consisting of tap water, bottled water, distilled water or saline solution.

7. The method as defined in claim 1, wherein said collection container is of a shape and size suitable to be held in the hand and to allow for collection of said sampling liquid as it falls from the mouth by gravity force, said collection container being held under the mouth with the head tilted forward.

8. The method as defined in claim 1, wherein said retrieved sampling liquid has a volume of at least about 2 ml.

9. The method as defined in claim 3, wherein said pH is determined by combining with said retrieved sampling liquid an appropriate amount of a pH indicator selected from the group consisting of pH indicator solution, pH indicator powder and pH indicator paper.

10. The method as defined in claim 9, wherein:
   (a) said pH indicator is bromothymol blue solution having a pH scale of about 6.0 to 7.6 pH units, with distinct color intervals of 0.2 pH units or less;
   (b) said bromothymol blue solution is added dropwise to said retrieved sampling liquid followed by periodic light agitation of said collection container to ensure mixing of said bromothymol blue solution with said retrieved sampling liquid; and
   (c) the resulting color of said retrieved sampling liquid is observed after a suitable period of time from addition of said bromothymol blue solution, through said collection container, to determine the pH of said retrieved sampling liquid by comparison of said color with a pH-color chart provided with said bromothymol blue solution.

* * * * *